(12) United States Patent
Dough

(10) Patent No.: US 9,332,780 B2
(45) Date of Patent: *May 10, 2016

(54) GELATED CRAB MEAT AND FOOD PRODUCTS DERIVED FROM GELATED CRAB MEAT

(76) Inventor: William Gabriel Dough, Manteo, NC (US)

( * ) Notice: Subject to any disclaimer, the term of this patent is extended or adjusted under 35 U.S.C. 154(b) by 534 days.

This patent is subject to a terminal disclaimer.

(21) Appl. No.: 13/563,779

(22) Filed: Aug. 1, 2012

(65) Prior Publication Data

US 2012/0308685 A1    Dec. 6, 2012

Related U.S. Application Data

(63) Continuation of application No. 11/788,768, filed on Apr. 20, 2007, now Pat. No. 8,287,935.

(60) Provisional application No. 60/812,771, filed on Jun. 12, 2006, provisional application No. 60/794,272, filed on Apr. 20, 2006.

(51) Int. Cl.
*A23L 1/31* (2006.01)
*A23L 1/325* (2006.01)
*A23L 1/314* (2006.01)
*A23L 1/33* (2006.01)

(52) U.S. Cl.
CPC .............. *A23L 1/3252* (2013.01); *A23L 1/3149* (2013.01); *A23L 1/31427* (2013.01); *A23L 1/33* (2013.01); *C12Y 203/02012* (2013.01)

(58) Field of Classification Search
CPC ..... A23L 1/3252; A23L 1/33; A23L 1/31427; A23L 1/3149
USPC ................. 426/643; 452/1, 6, 7, 8, 9, 10
See application file for complete search history.

(56) References Cited

U.S. PATENT DOCUMENTS

| | | |
|---|---|---|
| 1,385,951 A | 7/1921 | Range |
| 2,517,899 A | 8/1950 | Kenneth |
| 2,522,578 A | 9/1950 | Johnson |
| 2,546,517 A | 3/1951 | Harris et al. |
| 2,771,630 A | 11/1956 | Hiller |
| 2,771,631 A | 11/1956 | Hiller |
| 2,838,786 A | 6/1958 | Ward |
| 2,903,737 A | 9/1959 | Ward |
| 2,915,781 A | 12/1959 | Woolf et al. |

(Continued)

FOREIGN PATENT DOCUMENTS

JP          56-51979          5/1981

OTHER PUBLICATIONS

Fibrimex Product Concepts, "Portioning Breakthrough," FX Technology & Products LLC, Freemont, Nebraska, Nov. 2003.*

(Continued)

*Primary Examiner* — Vera Stulii
(74) *Attorney, Agent, or Firm* — Ben Schroeder Law PLLC

(57) ABSTRACT

Embodiments of the present invention relate to food products and methods and systems for producing such products. The food products of the present invention may include uncooked crab meat from species within Decopada Infrorders Anomura (i.e., King Crab and the like) and Brachyura Swimming Crabs and the like) that has been treated with an agent to promote gelation without cooking the meat.

28 Claims, 11 Drawing Sheets
(7 of 11 Drawing Sheet(s) Filed in Color)

(56) References Cited

U.S. PATENT DOCUMENTS

| | | | |
|---|---|---|---|
| 3,149,371 A | | 9/1964 | Anderson et al. |
| 3,151,351 A | | 10/1964 | Reinke |
| 3,201,022 A | | 8/1965 | Glidden et al. |
| 3,229,325 A | | 1/1966 | Amelang |
| 3,257,683 A | | 6/1966 | Rossnan |
| 3,325,856 A | | 6/1967 | Pack et al. |
| 3,712,821 A | | 1/1973 | Ronsivalli |
| 3,719,967 A | | 3/1973 | Craig |
| 3,921,256 A | | 11/1975 | Huebotter |
| 4,741,906 A | | 5/1988 | Paardekooper et al. |
| 4,816,278 A | * | 3/1989 | Sasamoto et al. ............. 426/513 |
| 5,431,938 A | | 7/1995 | Kou |
| 5,518,742 A | * | 5/1996 | Soeda et al. .................... 426/63 |
| 5,827,558 A | | 10/1998 | Corser et al. |
| 5,928,689 A | | 7/1999 | Milkowski et al. |
| 6,723,362 B1 | | 4/2004 | Rastogi |
| 2003/0161938 A1 | | 8/2003 | Johnston et al. |
| 2008/0081547 A1 | | 4/2008 | Phillips |

OTHER PUBLICATIONS

STIC Search Report, Feb. 2012 pp. 1-59.*
Activa. General Information, "Seafood Applications," Ajinomoto Food Ingredients LLC, Chicago, IL.
Activa. General Information, "Transglutaminase Basics," Ajinomoto Food Ingredients LLC, Chicago, IL.
Activa. General Information, "Regulatory Approvals," Ajinomoto Food Ingredients LLC, Chicago, IL.
Activa. General Information, "Activa in Red Meat Applications," Ajinomoto Food Ingredients LLC, Chicago, IL.
Activa. General Information, "Poultry Applications," Ajinomoto Food Ingredients LLC, Chicago, IL.
Crabmeat, Pasteurized Blue, Generic HACCP Plan, updated Jul. 15, 2002.
Fibrimex and Plasma Powder FG Application: Binding of fresh meat or fish. Sonac, a Sobel company, produced by Harimex Loenen, P.O. Box 50, NL-7370 AB Loenen, The Netherlands.
Fibrimex Product Concepts, "Concept Benefits" FX Technology & Products LLC, Freemont Nebraska.
Fibrimex Product Concepts, "Guidelines for Binding Meat using Fibrimex", FX Technology & Products LLC, Freemont Nebraska.
Fibrimex Product Concepts, "Portioning Breakthrough" FX Technology & Products LLC, Freemont Nebraska Nov. 2003.
Fibrimex Information, "What is Fibrimex?" FX Technology & Products LLC, Freemont, Nebraska, Jul. 2000.
Food Network: Culinary Q&A http//www.foodnetwork.com:80/food/cda/articleprint/0.,1983,FOOD_9796_1702217ARTICLE-DETAIL-PRINT.OO.html, Jan. 27, 2003.
Get It Together with Activa: An Innovative Way to Achieve Portion Control and Create Value-Added Products, Ajinomoto Food Ingredients LLC, Chicago, IL.
Gossett et al. "Quantitative Analysis of Gelatin in Egg Protien Systems," Food Technology, 1984, 38(5): 67-96.
Hartman, "The History of Blue Crab Harvest" Alabama Department of Conservation and Natural Resouces Marine Resources Division, Originally printed in Outdoor Alabama.
Hongsprabhas et al. "Use of Cold-Set Whey Protein Gelatin to Improve Poultry Meat Batters," 1999 Poultry Science, 78, 1074-1078.
Product Information: Applications and Use of Activa RM, Ajinomoto Food Ingredients LLC, Chicago, IL.
Product Information: Applications and Use of Activa FP, Ajinomoto Food Ingredients LLC, Chicago, IL.
Product Information: Applications and Use of Activa GB, Ajinomoto Food Ingredients LLC, Chicago, IL.
Product Information: Applications and Use of Activa TI and TI-U, Ajinomoto Food Ingredients LLC, Chicago, IL.
Product Information: "What is Fibrimex?" 2002, Society of Chemical Industry.
Suklim, Production of Restructured Squid and Scallops from Processing By-Products and Underutilized Species. Thesis VPI and State University Dec. 15, 1998.
United States International Trade Commission "Crabmeat From Swimming Crabs Investigation No. TA-201-71," Determination and Views of the Commisn. USITC Pub No. 3349, Aug. 2000.
"Use of Novel Dairy Ingredients in Processed Meats" http://www.teagasc.ie/research/reports.dairyproduction/4374/eopr-4374.htm as printed on Apr. 17, 2007.
Vance, Researcher works to develop low-fat cold bound restructured lamp chop suitable for boiling CSU Ag Research Initiative, CPSU, San Luis Obispo, 2004 ARI Pub #02-3-064.
http://www.foodtimeline.org/foodlobster.html#crab, Timeline and History of Crab from a culinary perspective, webpage accessed Apr. 4, 2008.
International Search Report for Patent Cooperation Treaty Serial Applicaiton No. PCT/US07/09697 mailed Jul. 9, 2008.
Written Opinion of the International Searching Authority for Patent Cooperation Treaty Serial Applicaiton No. PCT/US07/09697 mailed Jul. 9, 2008.
Prosecution History of Patent Cooperation Treaty Serial Applicaiton No. PCT/US07/09697.
Prosecution History of U.S. Appl. No. 11/788,768 (now U.S. Pat. No. 8,287,935).

* cited by examiner

GELATED CRAB MEAT AND FOOD PRODUCTS DERIVED FROM GELATED CRAB MEAT

RELATED APPLICATIONS

This application is a continuation of and claims priority to U.S. application Ser. No. 11/788,768, filed Apr. 20, 2007, which in turn claims priority to U.S. Provisional Patent Application 60/794,272, filed Apr. 20, 2006, and U.S. Provisional Patent Application 60/812,771, filed Jun. 12, 2006. The disclosure of U.S. application Ser. No. 11/788,768 and of U.S. Provisional Patent Applications 60/794,272 and 60/812,771 are incorporated by reference herein in their entireties.

FIELD OF INVENTION

The present invention relates to gelated crab meat and food products derived from gelated crab meat.

BACKGROUND

The meats of many species of Decapoda are highly valued seafood products, have been sustainable food sources for thousands of years, and comprise a multi-billion dollar segment of the overall global seafood industry. Within the infraorders Anomura and Brachyura are included the many commercial species of crab, Anomura includes the species commonly referred to as King Crab or Stone Crab. Brachyura includes all commercial species of crabs known as "Swimming Crabs" (e.g., *Sapidus* Blue Crab, *Portunus pelagicus* Blue Swimming Crab, *Scylla serrata* Mud Crab, *Portunus trituberculatus* 'Gazami').

Commercial species of Swimming Crabs are similar such that meat from one type of Swimming Crab may be considered to be directly interchangeable for the meat of another type of Swimming Crab both from a culinary standpoint, and in terms of market classification. Also, the standard commercial methods used for processing the meats of these species may be substantially the same, as the skeletal and muscular systems for each of the species are similar to each other.

Crabs are considered to be a delicacy, but may not be popular with some consumers due to the difficulty of extracting the meat from the shell. For example, although the meat in the claws is considered by many to be some of the highest quality meat in a crab, it can be quite difficult to get to the meat due to the thickness of the shell. Also, commercial processing of hard shelled crabs is complicated by the need to separate the meat from the shell. For example, when crabs are harvested they may be graded by size. The large crabs may be sold whole to restaurants and steam bars where they are generally cooked and eaten as whole crabs. Smaller crabs, however, may be sent to a picking house. Once in the picking house, the crabs may be steamed, and then the crabs are manually cracked and the meat is picked from the shell. This meat may be packaged and sold as pre-cooked crab meat.

Thus, uncooked crab meat is not generally used as a food source. It has not been considered feasible to extract raw crab meat in order to pre-cook and package the meat. Nor has it been considered commercially feasible to extract and sell crab meat as a raw product as is commonly done with virtually all other meats, whether from land or marine creatures. The unavailability of extracted uncooked crab meat is a global condition, and is the result of the nature of the crab's exoskeletal structure, combined with the fluid consistency of the crab meat, which makes the meat seemingly uneconomical to produce and use. Cooking the crab, by steaming/boiling while the crab is still alive, or soaking the crab in acid, can be used to cause the crab meat protein to denature and aggregate, thereby making extraction of the meat manageable. Thus, cooking the crab for treatment with acid) causes proteins to denature producing a 'chunky' meat that can be extracted (picked) from the shell and eaten. Cooked crabs can also be served whole, in which case the person eating the crab is required to remove the meat from the shell. This is a significant distinction from other seafood and meat products which are commonly processed and sold in their raw state.

Thus, there is a need to be able to utilize uncooked meat harvested from crabs. Also, based on the popularity of fish products, such as sushi, fish rolls, and the like, there is a need to provide uncooked crab meat that can be presented in a variety of forms such as nuggets, fillets, medallions or slices that may be made into various forms.

SUMMARY

Embodiments of the present invention relate to gelated crab meat and food products derived such gelated crab meat. The present invention may be embodied in a variety of ways.

In one embodiment, the present invention comprises a method for the preparation of crab meat for use in food products comprising obtaining uncooked meat from a crab and mixing the uncooked meat with at least one protein binding agent that promotes protein binding. The method may further comprise incubating the meat and the at least one protein binding agent under conditions such that proteins in the meat bind to each other and/or to proteins present in the binding agent to the extent that gelation of the meat occurs. In one embodiment, the method may also comprise incubating the meat and protein binding agent under conditions to produce a meat product that comprises a form that is substantially solid.

Other embodiments of the present invention comprise articles of manufacture comprising uncooked raw crab meat and at least one protein binding agent that promotes protein binding, wherein the at least one protein binding agent is added in an amount such that proteins in the meat and/or in the protein binding agent bind to each other to the extent that gelation of the crab meat occurs to form a gelated crab meat product.

Other embodiments and further details on various aspects of the present invention are set forth in the following description, figures, and claims. It is to be understood that the invention is not limited in its application to the details set forth in the following description, figures, and claims, but is capable of other embodiments and of being practiced or carried out in various ways.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1:
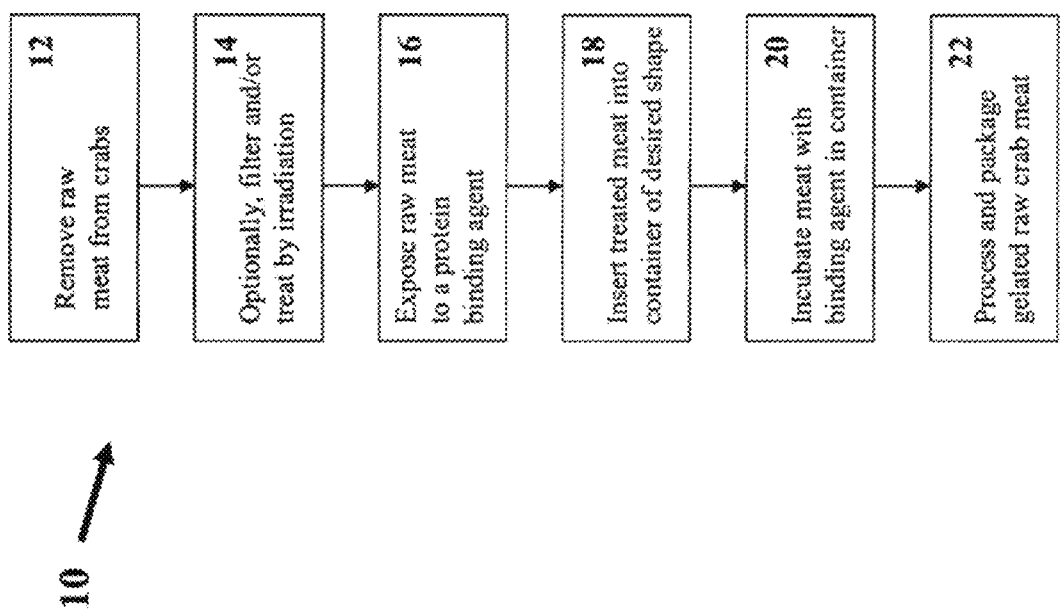
FIG. 1 shows a schematic representation of a method for treating crab meat with an agent that promotes protein binding and gelation according to one embodiment of the present invention.

As used herein, the term "gelated" describes the state of a meat product that has a continuous structure with permanent macroscopic dimensions over the useful product lifespan and solid-like rheological properties under static to low shear stress conditions. Also, the term "gelation" describes the creation of a three-dimensional network of bonded proteins where polymer-polymer and polymer-solvent interaction is balanced. Gelation is an orderly aggregation of proteins that form a three-dimensional network. In gelation, polymer-polymer and polymer-solvent interactions, as well as attractive and repulsive forces may be balanced such that a well-ordered matrix is formed.

As used herein, a protein binding agent (or a protein bonding agent) is a compound that promotes the binding of proteins to each other. The binding may comprise covalent bonds, protein crosslinking, and/or non-covalent interactions such as hydrophobic interactions, ionic interactions, or hydrogen bonds.

As used herein, protein binding for bonding) is the binding for bonding) of one protein to another. The binding may comprise covalent bonds, protein cross-linking, and/or non-covalent interactions such as hydrophobic interactions, ionic interactions, or hydrogen bonds.

As used herein, a "non-Newtonian fluid" is a fluid for which the relationship of shear stress and shear rate (F'/S) is not a constant.

As used herein, a material that is "pseudo-plastic" refers to a material that is substantially fluid and displays a decreasing viscosity with an increasing shear rate.

As used herein, a material that is plastic behaves as a solid under static conditions. A certain amount of force must be applied to the fluid before any flow is induced; this force is called the yield value. Once the yield value is exceeded and flow begins, plastic fluids may display Newtonian, non-Newtonian, pseudo-plastic, or dilatant flow characteristics.

As used herein, when referring to uncooked crab, the term "crab meat" or "meat" is defined as including the mixture of edible protein mass and proteinaceous fluids extracted from the crab, as much of the crab body fluids will contain protein. Crab meat does not include the shell or inner organs.

As used herein, the term "substantially solid" refers to something that holds its shape without an external support of the shape over time. Compositions that are substantially solid are not fluid, but retain their shape under static conditions (i.e., when not exposed to a shear force). Substantially solid materials include gels and gelated food products. For example, cooked egg white and formed gelatin are substantially solid.

As used herein, the term crab includes all crustaceans derived from the Decopada Infrorders Anomura crabs (e.g., King Crab and the like) or Brachyura crabs (e.g., Swimming Crabs and the like). Thus, the crab meat used in the methods, systems, and food products of the present invention may comprise meat from the blue crab (*C. sapidus*), Blue Swimming Crab (*Portunus pelagicus*), Horse Crab (*Portunus trituberculatus*), King Crab, Stone Crab, Dungeness crab, snow crab, tanner crab, coral crab, deep sea red crab, three spotted swimming crab, mud crab (mangrove crab). Or, other types of crab meat may be used.

As used herein, the term "soft separation" or "low pressure separation" is a term used in the art and refers to the procedure of extracting uncooked meat from a crab using a machine or device that works on the principle of pressing or squeezing the meat from uncooked crab while simultaneously separating, the soft tissue and fluids from the hard parts of the crab.

The anatomical characteristics of crab, and the economic costs associated with traditional processing of the meat from the crab species within Anomura and Brachyura have created an opportunity to use protein binding technology to produce a novel gelated seafood product that does not mimic any currently available forms of the meat from these species. Prior applications of protein binding technology to meat, e.g., as referred to in U.S. Pat. No. 4,741,906, incorporated by reference herein in its entirety, have focused on meats that have traditionally been commercially available in an uncooked state prior to the application of a protein binder, such as beef, pork, poultry, and fish. The applications generally have in common a focus on the bonding of proteins across the surface area of solid portions of the meat. Such bonding of meat parts is commonly referred to as meat restructuring. The resultant products are provided to mimic or create a direct substitute for a traditional (untreated) cut or form of the meat product from meat parts.

Uncooked crab meat is significantly different from these other meats. Uncooked crab meat is generally a viscous mass of proteins and natural fluids that can be described as a non-Newtonian pseudo-plastic fluid that under static conditions has a fixed volume without a fixed shape. The ability to use protein bonding as a way to gelate this meat is unique from typical restructuring applications.

Using a protein binding agent as a protein aggregator to create a gelated product that is comprised of solid and liquid proteins that have been gelated to form semi-rigid (e.g., substantially solid) three-dimensional network is a distinctly different application than the use of protein binding technology for the restructuring of smaller meat parts into larger units. The gelated crab meat of the present invention is therefore a new type of meat product. The ability to gelate raw crab meat has not been previously recognized due at least in part to the fluid nature of the meat when it is extracted from the crab.

The lack of uncooked crab meat in the marketplace has severely limited the ways in which crab meat can be prepared such that the market for extracted uncooked crab meat has not been realized. In various embodiments of the present invention, the ability to create a Related crab meat provides a market for new and innovative food products. A source of extracted uncooked crab meat that is gelated into a form that can be used for a variety of culinary applications (e.g., cut and otherwise handled with relative ease) provides for new uses for crab meat on a global scale. Such applications may be employed by chefs, for the creation of novel dishes, as well as for the use of crab in standard seafood dishes that have not previously been possible with crab. Also, in certain embodiments, the development of a market for gelated uncooked crab meat may allow for a manufacturing method with reduced costs and higher yields. In this way, the present invention may substantially increase the value of the raw material used in the crab industry. The new market for crab meat may thereby positively enhance the crab industry, which can be negatively impacted by under-utilization and waste of the raw material due to inefficiencies associated with the traditional crab processing methods. The ability to make uncooked crab meat useable by providing a gelated raw crab meat product with multiple culinary applications may lower costs and increase utilization of the natural resource. Thus, the present invention may increase utilization of raw crab meat extracted by the mechanical method of soft-separation. This methods of the present invention may facilitate the use of much less labor than traditional methods of processing cooked crab, and ma increase consumable meat yields from the crab by approximately 300% over yields associated with current processing methods.

Embodiments of the present invention comprise gelated crab meat, methods and systems for making gelated crab meat, and food products derived therefrom. The present invention may be embodied in a variety of ways.

In one embodiment, the present invention may comprise a method for the preparation of uncooked crab meat for use in food products. The method may comprise obtaining crab meat and mixing the crab meat with at least one protein binding agent that promotes binding of proteins in the crab meat. The proteins in the crab meat may bind either to other proteins in the meat, or to proteins in the protein-binding agent.

In certain embodiments, the protein-binding agent promotes gelation of the crab meat. The crab meat generally comprises both solid meat and body fluids that are rich in protein. Thus, in certain embodiments of the methods, systems and food products of the present invention, the protein binding agent may also interact with proteins present as solid meat, and with proteins present in the body fluids of the crab meat (and other solvent molecules), so as to form a three dimensional matrix or gel. The gel may therefore comprise both the solid and fluid proteins of the crab meat gelated into a substantially solid, form. Thus, in one embodiment, incubation of the protein binding agent is performed such that a three-dimensional network of bonded proteins is formed where polymer-polymer and polymer-solvent interactions are balanced (e.g. in equilibrium) to provide a stable gelated material.

The protein binding agent may comprise one active ingredient, or may comprise a plurality of active ingredients. For example, in one embodiment, the agent may comprise fibrinogen. Alternatively, the binding agent may comprise a mixture of fibrinogen and thrombin. Additionally or alternatively, the protein binding agent may comprise a transglutaminase (Tgase) enzyme. In yet other embodiments, non-crab proteins may be added. For example, in some embodiments, a caseinate may be used as part of the protein binding agent. Or, whey protein may be used as pan of the protein binding, agent. In yet other embodiments, actomyosin (e.g., seafood actomyosin) may be used as pan of the protein binding agent. Or, potato starch, functional pork protein, or functional soy protein may be used as part of the protein binding agent.

In certain embodiments, the method may further comprise incubating, the meat and the at least one protein binding agent to promote gelation under conditions to produce an uncooked meat product that comprises a substantially solid form. In an embodiment, the substantially solid form comprises a defined shape. For example, in one embodiment, the gelated crab meat may be formed into a cylindrical roll or a monolithic block. In certain embodiments, individual portions may be cut from the roll or the monolithic block. Or, the gelated crab meat may be formed as individual servings (i.e., gelated in the form of individual servings such as medallions, nuggets, patties and the like). Thus, in alternate embodiments, the substantially solid form is suitable for direct culinary use or mass processing.

Embodiments of the present invention may also comprise a method for the commercial utilization of raw crab meat. Thus, in certain embodiments, the present invention comprise to method for the preparation of uncooked crab meat for commercial use. In certain embodiments, the method may comprise the preparation of crab meat for use in food products comprising the steps of obtaining uncooked meat from a plurality of crabs and mixing the uncooked meat with at least one agent that promotes protein binding (i.e., a protein binding agent). The proteins in the crab meat may bind either to other proteins in the meat, or to proteins in the protein-binding agent. The method may also comprise incubating the meat and the at least one agent under conditions such that proteins in the meat aggregates to the extent that gelation occurs. Thus, in certain embodiments, the protein binding agent may also interact with proteins present as solid meat, and with proteins present in the body fluids of the crab meat (and other solvent molecules), so as to form a three dimensional matrix, or gel. The gel may therefore comprise both the solid and fluid proteins of the crab meat gelated into a substantially solid form. Thus, in one embodiment, incubation of the protein binding agent is performed such that a three-dimensional network of bonded proteins is formed where polymer-polymer and polymer-solvent interactions are balanced (e.g. in equilibrium) to provide a stable gelated material.

The method may comprise incubating the meat and protein aggregating agent under conditions to produce a meat product that comprises substantially solid form. In an embodiment, the substantially solid form comprises a defined, shape. For example, in one embodiment, the gelated crab meat may be formed into a cylindrical roll or a monolithic block. In certain embodiments, individual portions may be cut from the roll or the monolithic block. Or, the gelated crab meat may be formed as individual servings such as medallions, nuggets, patties and the like. Thus, in alternate embodiments, the substantially solid form is suitable for direct culinary use or mass processing.

Also, the method may comprise distributing the raw crab meat for sale. The crab meat may be distributed to a marketing unit or end user. For example, a marketing unit may comprise a seafood distributorship, a seafood store, or a retail food market (e.g., grocery stores or restaurants). An end user may comprise a restaurant and/or a consumer. Thus, the method may comprise distributing the gelated crab meat to at least one entity (e.g., seafood stores, seafood distributors, or consumers) for selling or using the gelated crab meat either in bulk form, or as individual servings. In one embodiment, bulk form refers to an amount of gelated crab meat that comprises a plurality of servings. In an embodiment, a bulk form comprises an amount of gelated crab meat that comprises a plurality of servings. In other embodiments, the method may comprise forming or cutting the gelated meat into desired semi-solid semi-rigid shapes that can be packaged, processed and portioned as a cohesive unit with a functional three dimensional structure.

The gelated raw crab meat made with the methods of the present invention may comprise an increase in viscosity as compared to ungelated crab meat. In certain embodiments, the gelated crab meat may comprise increase in viscosity of at least 100% (i.e., a 2-fold increase) as compared to untreated crab meat when measured at a shear stress of 2 revolutions per minute (RPM). In alternate embodiments, the gelated crab meat may comprise increase in viscosity of at least 3-fold, or at least 4-fold, or at least 5-fold, or at least 10-fold, or at least 15-fold, or at least 20-fold, or at least 25-fold, or at least 10-fold, or at least 35-fold, or at least 40-fold, or at least 50-fold, or at least 60-fold as measured at a shear stress within the range of from about 2 to 20 RPM (e.g., 2, 4, 10, 20 RPM or other shear stress values within this range). Thus, in alternate embodiments, the gelated crab meat may comprise a fold increase in viscosity ranging from about 2-60, or 2-50, or 2-30, or 2-30, or 3-30, or 3-25, or 3-20, or 3-15, or 3-10, or 3-5, or 4-30, or 4-25, or 4-20, or 4-15, or 4-10, or 4-5, or 5-30, or 5-25, or 5-20, or 5-15, or 5-10 fold, or other values within these ranges, depending upon the shear stress used. In certain embodiments, the shear stress may range from about 2 to 20 RPM (e.g., 2, 4, 10, 20 RPM or other shear stress values within this range).

Other embodiments of the present invention may comprise systems for the preparation of uncooked crab meat for use as a food product. The system may comprise a station for mixing uncooked crab meat with at least one protein binding agent that promotes protein-protein binding. The protein binding agent may promote binding of proteins in the crab meat. The proteins in the crab meat may bind either to other proteins in the meat (e.g., the solid meat and/or the proteinaceous body fluids), and/or to proteins in the protein-binding agent.

In certain embodiments, the protein-binding agent promotes gelation of the crab meat. Thus, the protein binding agent may also interact with proteins present as solid meat, and with proteins present in the body fluids of the crab meat (and other solvent molecules), so as to form a three dimensional matrix or gel. The gel may therefore comprise both the solid and fluid proteins of the crab meat gelated into a substantially solid form. Thus, in one embodiment, incubation of the protein binding agent is performed such that a three-dimensional network of bonded proteins is formed where polymer-polymer and polymer-solvent interactions are balanced (e.g. in equilibrium) to provide a stable gelated material.

The agent may comprise one active ingredient, or may comprise a plurality of active ingredients. For example, in one embodiment, the agent comprises a mixture of fibrinogen and thrombin. Alternatively, the protein binding agent may comprise a transglutaminase (Tgase) enzyme. In yet other embodiments, non-crab proteins may be added. For example, in some embodiments, a caseinate may be used as part of the protein binding agent. Or, whey protein may be used as part of the protein binding agent. In yet other embodiments, actomyosin (e.g., seafood actomyosin) may be used as part of the protein binding agent. Or, potato starch, functional pork protein, or functional soy protein may be used as part of the protein binding agent. In certain embodiments, the method may further comprise incubating the meat and the agent to promote gelation under conditions to produce an uncooked meat product that comprises a distinct shape and form.

Also, the system may comprise a station for incubating the meat and the protein binding (i.e., gelation-promoting) agent or agents under conditions to produce a meat product that comprises a shape and thrill that can be packaged, processed, and/or portioned as a cohesive unit with a functional three dimensional structure. In certain embodiments, the system may also comprise a station for obtaining uncooked meat from a crab. In one embodiment, the meat may be extracted from the crabs using a machine or device that works on the principle of pressing or squeezing the meat from the crab, in certain embodiments, the crab meat may be extracted using the technique referred to as soft separation or low pressure separation.

The gelated raw crab meat made with the systems of the present invention may comprise an increase in viscosity as compared to ungelated crab meat. In certain embodiments, the gelated crab meat may comprise increase in viscosity of at least 100% (i.e. a 2-fold increase) as compared to untreated crab meat when measured at a shear stress of 2 revolutions per minute (RPM). In alternate embodiments, the gelated crab meat may comprise increase in viscosity of at least 3-fold, or at least 4-fold, or at least 5-fold, or at least 10-fold, or at least 15-fold, or at least 20-fold, or at least 25-fold, or at least 30-fold, or at least 35-fold, or at least 40-fold, or at least 50-fold, or at least 60-fold as measured at a shear stress within the range of from about 2 to 20 RPM (e.g., 2, 4, 10, 20 RPM or other shear stress values within this range). Thus, in alternate embodiments, the gelated crab meat may comprise a fold increase in viscosity ranging from about 2-60, or 2-50, or 2-30, or 2-30, or 3-30, or 3-25, or 3-20, or 3-15, or 3-10, or 3-5, or 4-30, or 4-25, or 4-20, or 4-15, or 4-10, or 4-5, or 5-30, or 5-25, or 5-20, or 5-15, or 5-10 fold, or other values within these ranges, depending upon the shear stress used. In certain embodiments, the shear stress may range from about 2 to 20 RPM (e.g., 2, 4, 10, 20 RPM or other shear stress values within this range).

In yet other embodiments, the present invention comprises articles of manufacture that comprise meat products made using the methods and the systems of the present invention. In certain embodiments, the food product may comprise crab meat that is gelated prior to cooking. The food product may comprise uncooked crab meat with at least one protein binding agent that promotes protein-protein binding. The proteins in the crab meat may bind either to other proteins in the meat, or to proteins in the protein-binding agent. For example, embodiments of the present invention comprise an article of manufacture comprising uncooked raw crab meat and at least one protein binding agent that promotes protein binding, wherein the at least one protein binding agent is added in an amount such that proteins in the meat and/or in the protein binding, agent bind to each other to the extent that gelation of the crab meat occurs to form a gelated crab meat product.

In certain embodiments, the protein-binding agent promotes gelation of the crab meat. Thus, in certain embodiments, the protein binding agent may also interact with proteins present as solid meat, and with proteins present in the body fluids of the crab meat (and other solvent molecules), so as to form a three dimensional matrix or gel. The gel may therefore comprise both the solid and fluid proteins of the crab meat gelated into a substantially solid form. Thus, in one embodiment, incubation of the protein binding agent is performed such that a three-dimensional network of bonded proteins is formed where polymer-polymer and polymer-solvent interactions are balanced (e.g. in equilibrium) to provide a stable gelated material.

The agent may comprise one active ingredient, or may comprise a plurality of active ingredients. For example, in one embodiment, the agent comprises a mixture of fibrinogen and thrombin. Alternatively, the protein binding agent may comprise a transglutaminase (Tgase) enzyme. In yet other embodiments, non-crab proteins may be added. For example, in some embodiments, a caseinate may be used as part of the protein binding agent. Or, whey protein may be used as part of the protein binding agent. In yet other embodiments, actomyosin (e.g., seafood actomyosin) may be used as part of the protein binding agent. Or, potato starch, functional pork protein, or functional soy protein may be used as part of the protein binding agent. In certain embodiments, the method may further comprise incubating the meat and the agent to promote gelation under conditions to produce an uncooked meat product that comprises a distinct shape and form.

The gelated raw crab meat may comprise an increase in viscosity as compared to ungelated crab meat. In certain embodiments, the gelated crab meat may comprise increase in viscosity of at least 100% (i.e., a 2-fold increase) as compared to untreated crab meat when measured at a shear stress of 2 revolutions per minute (RPM). In alternate embodiments, the gelated crab meat may comprise increase in viscosity of at least 3-fold, or at least 4-fold, or at least 5-fold, or at least 10-fold, or at least 15-fold, or at least 20-fold, or at least 25-fold, or at least 30-fold, or at least 35-fold, or at least 40-fold, or at least 50-fold, or at least 60-fold as measured at a shear stress within the range of from about 2 to 20 RPM (e.g., 2, 4, 10, 20 RPM or other shear stress values within this range). Thus, in alternate embodiments, the gelated crab meat may comprise a fold increase in viscosity ranging from about 2-60, or 2-50, or 2-30, or 2-30, or 3-30, or 3-25, or 3-20, or 3-15, or 3-10, or 3-5, or 4-30, or 4-25, or 4-20, or 4- 15, or 4-10, or 4-5, or 5-30, or 5-25, or 5-20, or 5-15, or 5-10 fold, or other values within these ranges, depending upon the shear stress used. In certain embodiments, the shear stress may range from about 2 to 20 RPM (e.g., 2, 4, 10, 20 RPM or other shear stress values within this range).

In certain embodiments, the gelated crab meat is provided in a variety of forms that may comprise unique culinary applications for crab. Many culinary applications that have not been regarded as practical for crab in its currently available forms (i.e., packaged cooked meat or whole crab) ma be applicable for gelated crab meat. Thus, embodiments of the present invention comprise the generation eta crab meat product that may be used for sautéing, grilling, poaching, frying, forming, making of sausages, paddies, steaks, or for use as wrappers, and the like. The crab meat products may thus be provided as bulk crab meat products, such as rolls or blocks of crab meat from which individual portions may be sectioned. Or, the crab meat products may be formed as individual servings such as medallions, patties, fillets, strips, and the like.

In the methods, systems and food products of the present invention, gelation may be performed prior to cooking the meat in one embodiment, the non-gelated uncooked crab meat has the consistency of a viscous pseudo-plastic. Thus, the method may also comprise the step of extracting uncooked meat from a crab. In an embodiment, soft separation or a similar procedure is used to obtain the raw (uncooked) crab meat.

Each of the methods, systems, and food products of the present invention may, in certain embodiments, comprise incubating the meat and the agent to promote gelation under conditions to produce an uncooked meat product that comprises a substantially solid form. In certain embodiments, the meat and at least one protein binding agent are incubated under conditions to produce a meat product that comprises a defined shape. In alternate embodiments, the form of the gelated crab meat is suitable for culinary use or mass processing and packaging in certain embodiments, the gelated crab meat comprises a monolithic unit that can be portioned into unit sizes suitable for individual servings. For example, the defined shape may comprise a cylindrical shape. Where the bulk gelated crab meat comprises a cylinder, the cylindrical shape may be cut into slices by cutting the cylinder perpendicular to the longitudinal axis of the cylinder. Or, the gelated crab meat may be formed or gelated as individual portions.

For each of the methods, systems or food products of the present invention, forming, the meat into a distinct shape may comprise thrilling or cutting the meat into desired semi-solid semi-rigid shapes that can be packaged, processed and portioned as a cohesive unit with a functional three dimensional structure. In one embodiment, the crab meat may be formed into a substantially cylindrical shape (e.g., a roll or log) from which individual servings may be cut. For example, medallions may be cut from cylinders baying a diameter of from about 1-3 inches, slices and/or patties may be cut from cylinders having a diameter from about 2.5 to 6 inches, and fillets may be cut from cylinders having a diameter of from about 5 to 10 inches.

Or, the gelated crab meat may be formed as individual portions. For example, the gelated crab may be formed in a container that is shaped to hold individual crab medallions or patties. In this way, the crab may be formed and packaged in a single step (or at a single station).

Various amounts of the protein binding agent may be added as required. In alternate embodiments, the protein bonding agent comprises about 0.05-20%, or 0.1-10%, or 1-10%, or 4-9%, 5-8% of the meat product for a fibrin-based agent or, 0.4-1.4%, 1.4-3%, 0.75-2.5% of a of the meat product for a Tgase-based agent. In alternate embodiments, the protein binding agent may comprise from about 0.05-25%, 0.05-20%, 1-20%, 0.1-10%, 0.5-10%, 2-15%, 3-15%, 1-10%, 4-9%, 4-8%, 1-5%, 5-8%, or about 6%, or 0.4-7%, 0.7-1.4%, 1-3%, 0.4-1.4%, 1.4-3%, 0.75-2.5%, 0.05-2.5%, 0.75 to 3%, 1-2%, 2-3% or 3-5% depending upon the nature of the protein binding agent used.

In certain embodiments of the methods, systems and food products of the present invention, the meat may be cold pasteurized or treated with preservatives prior to the addition of the agent that promotes protein aggregation. This may be done either before or after addition of the protein binding agent to the raw crab meat (e.g., before or after gelation). For example FDA approved preservatives such as sulfur dioxide, potassium hydrogen sulfite, sodium EDTA, BHA, BHT, sodium nitrate, and the like may be used. For example, in certain embodiments, the crab meat may be gelated, and then the packaged gelated crab subjected to irradiation as a means of cold pasteurization.

In alternate embodiments of the methods, systems, and food products of the present invention, the crabs may comprise Decopada Infrorders Anomura crabs (e.g., King Crab and the like) or Brachyura crabs (e.g., Swimming Crabs and the like). Thus, the crab meat used in the methods, systems, and food products of the present invention may comprise meat from the blue crab (*C. sapidus*). Blue Swimming Crab (*Portunus pelagicus*). Horse Crab (*Portunus trituberculatus*), King Crab, Stone Crab, Dungeness crab, snow crab, tanner crab, coral crab, deep sea red crab, three spotted swimming crab, mud crab (mangrove crab). In alternate embodiments, the crab may comprise a *Portunus trituberculatus* 'Gazami' a king crab, a spiny spider crab, a swimming crab, a gazami, or a stone crab. Or, other types of crab meat may be used. The crab meat used for the methods, systems, and food products of the present invention may be derived from an entire organism or only a portion of the organism. In one embodiment, the portion of the organism comprises a claw or a leg of the crab. In another embodiment the portion of the organism may comprise the body, or a portion of the body of the crab.

An example method of the present invention is illustrated in FIG. 1. Thus, in an embodiment, the method 10 may comprise a first step 12 of extracting meat from a crab. Also, in certain embodiments, the method may comprise treating or filtering the meat to reduce any possible contamination by pathogens and/or particulates 14. For example, the method may comprise straining, filtering, adding preservatives and/or cold pasteurizing the meat.

The method may also comprise a step 16 for mixing the meat with at least one agent that promotes gelation. The method may comprise obtaining crab meat and mixing the crab meat with at least one protein binding agent that promotes protein-protein binding. In an embodiment, the agent provides for binding of proteins that are in the agent itself. Additionally, or alternatively, the protein binding agent may facilitate cross-linking of proteins in the crab meat. In an embodiment, the protein-binding agent promotes elation of the crab meat. As described herein, the agent may comprise one active ingredient, or may comprise a plurality of active ingredients. For example, in one embodiment, the agent comprises a mixture of fibrinogen and thrombin. Alternatively, the protein binding agent may comprise a transglutaminase (Tgase) enzyme. In yet other embodiments, non-crab proteins may be added such as caseinate, whey protein, actomyosin, or soy protein.

Once the meat has been treated, it may be shaped and set into a form that allows for the gelled product to be portioned, packaged and used as a food product. For example, the meat may be shaped to form rolls that may be sliced into steaks or thin sheets. Thus, the method may comprise inserting the treated meat into a container to shape the final product 18. Once the meat has been mixed with the protein binding, agent, and in some cases packaged into a processing container, it may be incubated for a period of time, and at an appropriate temperature with the at least one agent to promote gelation 20. For example, the meat may be chilled (e.g., brought to a temperature of about 34 to 44 degrees Fahrenheit or 1 to 7 degrees Celsius) and mixed thoroughly with the protein binding agent. In an embodiment, the meat may be chilled to a temperature of less than 10° C. For example, in alternate embodiments, the meat may be chilled to a temperature of from about 1° C. to 7° C., 1° C. to 5° C., or from about 2° C. to 4° C. Where the processed meat requires a specific shape, the treated meat may be stuffed into containers that will mold the final product as desired. The meat and the protein binding agent may be incubated for a timed and at a temperature (e.g., in a cooler at 2° C. to 4° C.) to promote gelation. The meat may be incubated for a period sufficient to induce gelation. In alternate embodiments, the meat may be incubated with the gelation agent for about 30 minutes, or about 1 hour, or about 2 hours, or about 3 hours, or about 4 hours, or about 5 hours, or about six hours. In one embodiment, the meat may be incubated with the gelation agent for about 6 to 8 hours. For example, the meat may be incubated overnight at 2-4° C. in the presence of the protein binding agent. The meat may be removed from its mold to be stored or stored in its mold indefinitely. In some cases the mold may also serve as packaging. Also in some cases the molding may be an edible part of the product.

Once the meat has been incubated under conditions that are sufficient for gelation to occur, the meat may then be processed in various ways including being cut into desired shapes and sizes or otherwise portioned, frozen, refrigerated, cooked and/or packaged 22.

Figure 2:
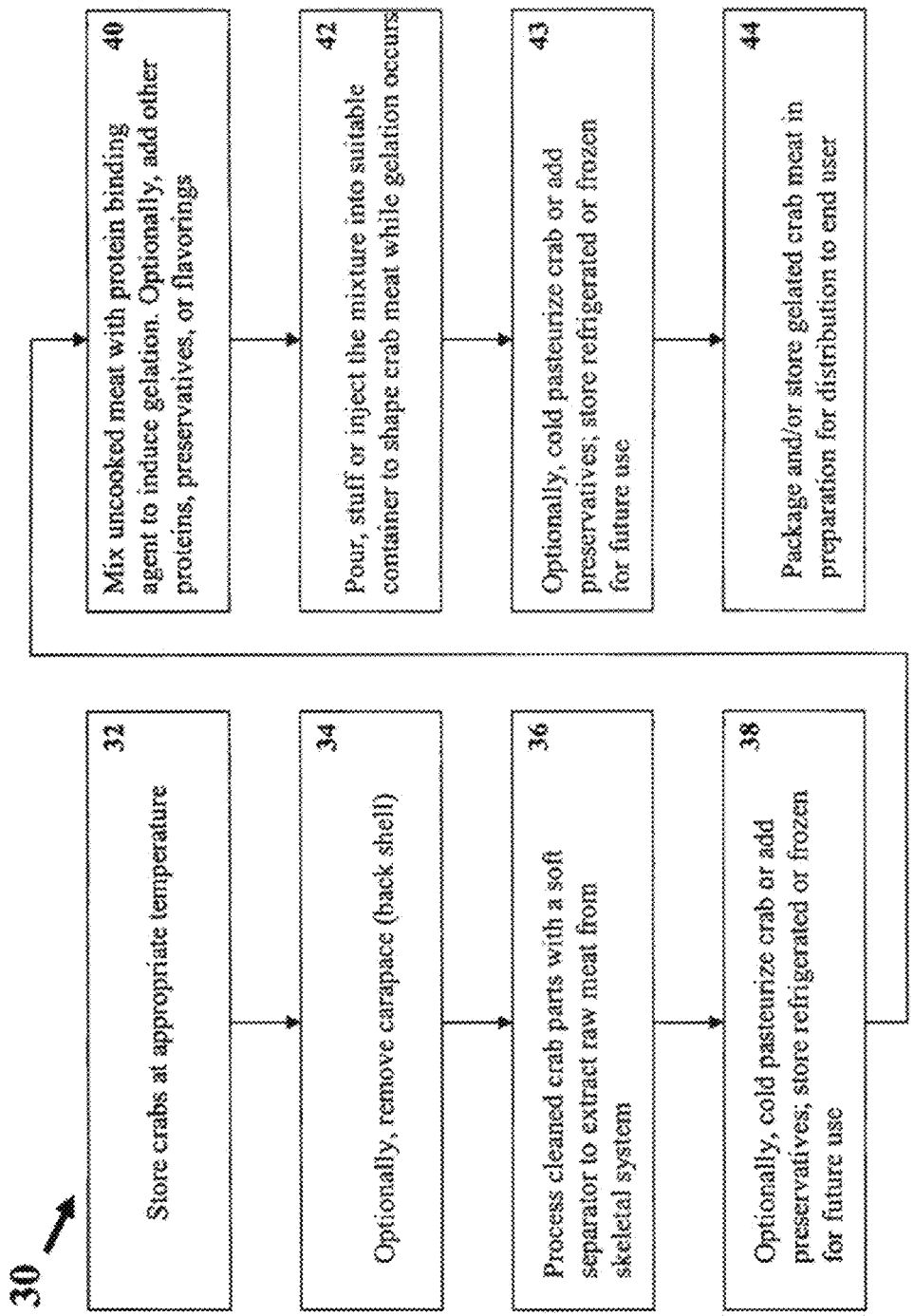
FIG. 2 shows an alternate schematic representation of a method for treating crab meat with an agent that promotes binding and gelation according to one embodiment of the present invention.

FIG. 2 shows an alternate embodiment of a method 30 for producing gelated crab meat food products of the present invention. Thus, as shown in FIG. 2, once the crabs have been caught, they may be stored at an appropriate temperature per industry standards 32 (e.g., frozen or kept alive in a refrigerated, environment, on ice, or in water). Next, the carapace (back shell) of the crab may be removed by hand, or by machine 34. The crab parts may next be mechanically processed to extract or isolate the raw meat from the skeletal system 36. For example, in one embodiment, raw crab meat is extracted from the crab using a soft separator or similar mechanism.

The crab meat may then optionally be treated or strained to remove any pathogens and/or particulates 38. In an embodiment, the meat may be cold pasteurized or irradiated to remove pathogens. Additionally or alternatively, the crab meat may be treated with additives such as salt, preservatives, flavorings etc. For example, preservatives may be added to inhibit pathogen growth or as an antioxidant. Flavoring and salt may be added to produce a desired flavor profile. The raw crab meat may then be stored in the cold (e.g., in a cooler or cool room) or frozen until further processing.

Once the amount of meat that is needed for processing as the food product(s) of interest has been obtained, the raw meat may be treated with an agent or agents that promotes protein-protein binding and gelation of the meat. The meat may be mixed, i.e., either by hand or using an automated mixer, with the protein binding agent using proportions required to promote gelation as described herein. During the mixing of the raw meat with the protein binding agent(s), additives are not required, but may be added. Example additives may include preservatives and/or flavorings to enhance the taste and maintain the freshness of the meat. Also, additives may include salts, fillers, buffers, or other compounds that may support the gelation method. For example the addition of salts with sodium, calcium or potassium cations may act as preservatives as well as a buffer against changes in pH based on the associated anion. Also, other animal or vegetable proteins and extracts such fish meat or extract, shellfish meat or extract, crustacean meat or extract, whey, soy and dairy may be added to form a mix with the gelated crab protein to act as fillers or to change flavor and texture profiles.

After mixing the crab meat with the protein binding agent, the meat may be formed during setting by insertion into a wrapping, casing, mold or other type of container that will set the meat in the final shape that is desired. For example, the meat may be quad into a tube, if the final product is to be cylindrical in shape. The meat may then be incubated in the container under conditions that allow for a gel with a definite shape to form through a reaction with the protein bonding agent. Once the meat has gelled to form the final shape, the wrapping or container may be removed and the meat further processed as desired. Thus, the gelled meat may be portioned, cooked or frozen as desired. For example, in an embodiment, the gelled meat may be sliced into thin slices, or chopped to form nuggets, medallions, steaks, patties, and the like.

A variety of molds, casings and packaging may be used to shape the meat. Examples may include casings certified for use in the food industry and may be artificial or natural casings, permeable or impermeable casings. These casing may be removed during the production process or used as packaging. Molds may be made from plastic, metal, paper, glass, ceramic, or other material safe for use in the food industry. Molds may take various shapes and can be used to produce small individual servings or larger forms that are liner portioned. Molds ma be removed during the production process or used as packaging. Molds, casings and packagings may constitute an edible part of the product. For example, the crab may be cast in a mold, wrap or casing made from vegetable, fish, pork, beef, poultry, crystallized sugar or salt, dough, grains, and other edible substances.

In certain embodiments, the meat may be cold pasteurized or irradiated to remove pathogens after it has been incubated with the protein binding agent 43. For example, the meat may be irradiated after it has been packaged into a container for shipping. Additionally or alternatively, the crab meat may be treated with additives such as salt, preservatives, flavorings etc. For example, preservatives may be added to inhibit pathogen growth or as an antioxidant. Flavoring and salt may be added to produce a desired flavor profile. The raw crab meat may then be stored in the cold (e.g., in a cooler or cool room) or frozen in preparation for distribution to an end user 44.

A variety of agents to promote protein-protein binding and gelation may be used for the methods and systems of the present invention, and in the food products made with the methods and systems of the present invention. In an embodiment, the agent to promote gelation may comprise fibrinogen. In one embodiment, the agent may comprise a mixture of animal fibrinogen and thrombin as described in U.S. Pat. No. 4,741,906. For example, the agent may comprise the commercially available products FIBRIMEX® and/or Plasma Powder FG commercially available from FX Technology & Products, LLC (Fremont, Nebr.) and Harimex (Loenen, Netherlands). FIBRIMEX® and Plasma Powder FG allow for the binding of raw meat materials to form larger products by the fibrin-mediated cross-linking of proteins catalyzed by fibrinogen and thrombin. Thus, in alternate embodiments, either FIBRIMEX® and/or Plasma Powder FG may be used as a protein binding agent to promote the gelation of uncooked crab meat.

In certain embodiments, the FIBRIMEX® may be reconstituted as recommended by the manufacturer and mixed with the raw meat. The meat may be chilled and mixed thoroughly with the protein binding agent. In an embodiment, the meat may be chilled to a temperature of less than 10° C. For example, the meat may be chilled to a temperature of about 34 to 44 degrees Fahrenheit (i.e., 1 to 7 degrees Celsius). For example, in alternate embodiments, the meat may be chilled to a temperature of from about 1° C. to 7° C., 1° C. to 5° C. or from about 2° C. to 4° C. Where the processed meat requires a specific shape, the treated meat (e.g., raw meat mixed with FIBRIMEX®) may be stuffed into containers that will mold the final product as desired. The meat and FIBRIMEX® may be incubated for a time and at a temperature (e.g., in a cooler at 2° C. to 4° C.) to promote gelation. The meat may be incubated for a period sufficient to induce protein binding and/or gelation. In alternate embodiments, the meat may be incubated with the at least one protein binding agent for about 30 minutes, or about 1 hour, or about 2 hours, or about 3 hours, or about 4 hours, or about 5 hours, or about six hours. In one embodiment, the meat may be incubated with the at least one protein binding agent for about 6 to 8 hours. However, gelation may be visible within 30 minutes. For example, the meat may be incubated overnight at 2-4° C. in the presence of the FIBRIMEX®. The amount of the gelation agent may be varied depending on the state of the raw meat (e.g., moisture content, temperature, type of crab meat being used), and the processing parameters (e.g., time and temperature of incubation; amount of meat being processed). For example, in alternate embodiments. FIBRIMEX® may be used in a range of from 0.05-20%, 0.1-10%, or from 1-10%, or from 4-9%, or from 5-8% or about 6% of the mixture (i.e., crab meat and FIBRIMEX®) composition. Ranges within these ranges may also be used.

In an alternate embodiment, products such as Plasma Powder FG may be used. Plasma Powder FG is a powder containing an increased fibrinogen concentration and is produced from beef or porcine plasma. In an embodiment, Plasma Powder FG may be mixed into the uncooked crab meat as a powder to promote gelation. The treated meat may then be inserted into a container (e.g., casing or mold) providing the desired shape of the meat after gelation. The meat may then be incubated under conditions to promote gelation. For example, in certain embodiments, the meat may be brought to a temperature of about 34 to 44 degrees Fahrenheit or 1 to 7 degrees Celsius. In alternate embodiments, the meat may be chilled to a temperature of less than 10° C. For example, in one embodiment, the meat may be chilled to a temperature of from about 1° C. to 7° C., 1° C. to 5° C., or from about 2° C. to 4° C. The meat may be incubated for a period sufficient to induce protein binding and/or gelation. In alternate embodiments, the meat may be incubated with the at least one protein binding agent for about 30 minutes, or about 1 hour, or about 2 hours, or about 3 hours, or about 4 hours, or about 5 hours, or about six hours. In one embodiment, the meat may be incubated with the at least one protein binding agent for about 6 to 8 hours. For example, the meat may be incubated overnight at 2-4° C. in the presence of the Plasma Powder FG. In an embodiment, the meat is incubated at 0-4° C. for at least 6 hours. At this point, the protein bonding reaction may be complete, such that the meat may be further processed (e.g., sliced, diced, made into nuggets) prior to freezing, cooking and/or packaging.

For the application of Plasma Powder FG as a liquid, the powder may be blended with the correct amount of ice water as per the manufacturer's instructions and mixed with the raw meat. In one embodiment, about 4 parts ice/water per part Plasma Powder FG powder is used. Again, in an embodiment, the treated meat may then be inserted into a container (e.g., casing or mold) providing the desired shape of the meat after gelation. The meat may then be incubated under conditions to promote gelation (e.g., 0-4° C. for at least 6 hours). At this point, the protein binding reaction may be complete, such that the meat may be further processed (e.g., sliced, diced, made into nuggets) prior to freezing, cooking and/or packaging. In alternate embodiments, the Plasma powder FG is used in a range of from 0.05-5%, 0.1-3%, or from 1-3%, or from 1-2%, or from 2-3%, or from 0.3-2%, or from 0.3-1%, or from 0.4-0.7%, or from 0.7% to 1.4%, of total product composition. Ranges within these ranges may also be used.

In yet another embodiment, a protein binding agent comprising bacterial transglutaminase (Tgase) may be adapted to promote gelation. In an embodiment, the Tgase may comprise a caseinate, maltodextrin, hydrolyzed milk protein or other ingredients as aggregator matrix substrates. Also, in an embodiment, the Tgase-based protein binding agent may comprise seafood actomyosin as an aggregator matrix substrate. In an embodiment, the Tgase/caseinate (and optionally, maltodextrin, hydrolyzed milk protein, gelatin, whey protein and/or actomyosin) may be blended with ice water and mixed with the raw meat. Again, in an embodiment, the treated meat may then be inserted into a container (e.g., casing or mold) providing the desired shape of the meat after gelation. The meat may then be incubated under conditions to promote protein binding and/or gelation. In certain embodiments, the meat may be brought to a temperature of about 34 to 4.4 degrees Fahrenheit or 1 to 7 degrees Celsius. For example, in alternate embodiments, the meat may be chilled to a temperature of less than 10° C. For example, in alternate embodiments, the meat may be chilled to a temperature of from about 1° C. to 7° C., 1° C. to 5° C., or from about 2° C. to 4° C. The meat may be incubated for a period sufficient to induce protein binding and/or gelation. In alternate embodiments, the meat may be incubated with the protein binding agent for about 30 minutes, or about 1 hour, or about 2 hours, or about 3 hours, or about 4 hours, or about 5 hours, or about six hours, in one embodiment, the meat may be incubated with the protein binding agent for about 6 to 8 hours. In one embodiment, the meat may be incubated with the Tgase-based binding agent (and any additional binding, agents) overnight. In an embodiment, the meat is incubated at 0-4° C. for at least 6 hours. At this point, the protein binding reaction may be complete, such that the meat may be further processed (e.g., sliced, diced, made into nuggets) prior to freezing, cooking and/or packaging.

In alternate embodiments, the Tgase-based protein binding agent is used in a range of from 0.5-20%, 0.1-10%, 0.75% to 3%, 1 to 2%, or from 2-3%, or from 3-5% of total product composition. In alternate embodiments, the Tgase enzyme may be used in amounts ranging from 100-3000 E/Kg meat, or from 200-2000 EU/kg meat, or from 300-1,500 EU/kg meat, or from 400-1,000 EU/kg meat, or from 500-900 EU/kg meat. In an embodiment about 500-700 EU/kg meat of Tgase is used. Use of the Tgase may require higher levels of protein (about 15% or more). Ranges within these ranges may also be used.

In some embodiments, other protein binding agents may used to induce gelation of the raw crab meat to make the food products of the present invention. Thus, in alternate embodiments, protein binding and/or gelation agents such as whey protein concentrate (WPC), potato starch (PS), functional pork protein (FPP), and/or functional soy protein concentrate (FSPC) may be used. These additional protein binding agents may be used in a range of from 0.05-25%, 1-20%, or from 2-15%, or from 3-15% of total product composition. Ranges within these ranges may also be used.

In yet another embodiment the protein binding agent comprising bacterial transglutaminase (Tgase) may be a product available from Ajinomoto Inc, or its subsidiaries. These products may include any one or combination of the Tgase products included in the Activa product line and may be used in concentrations ranging from 0.5-20%, 0.1-10%, 0.75% to 3%, 1 to 2% or from 2-3%, or from 3-5% of total product composition. Activa may be used as a slurry by pre-hydrating the powder at about 4 to 4.5 times its weight in water or as a dry powder. The Activa slurry or dry powder is mixed into the uncooked crab meat and processed in accordance with the embodiment describing the use of (Tgase).

Figure 3:
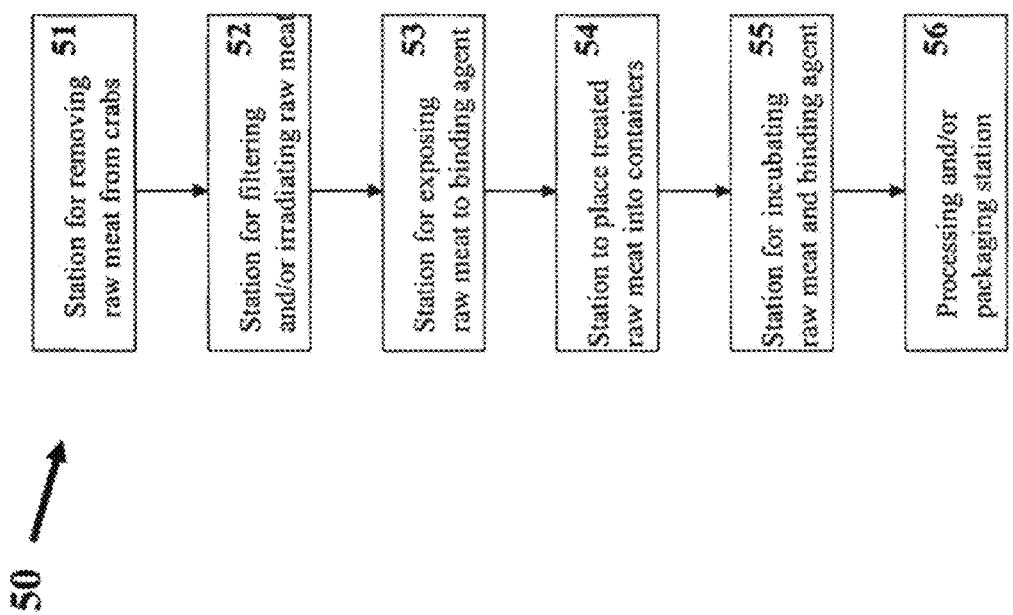
FIG. 3 shows a schematic representation of a system for treating crab meat with an agent that promotes binding and gelation according to one embodiment of the present invention.

Other embodiments of the present invention may comprise systems for the preparation of uncooked crab meat for use in food products. An example system of the present invention is illustrated in FIG. 3. Thus, in an embodiment, the system 50 may comprise a station 51 for obtaining uncooked meat from a crab. This may be done by running the crab or its parts through a machine that work as a soft separator as is predefined. The meat is then collected from the machine in and stored in a food grade plastic, metal, or glass container for storage or use in the next step.

Also, in certain embodiments, the system may comprise a station for filtering, straining, or treating the meat to reduce any possible contamination by pathogens and/or particulates 52. For example, the meat may be spread across a metal or polymer screen having a mesh size of 1 to 10 mm and subsequently scraped, pushed, pulled or drawn through the screen effectively separating the meat from any larger particles left in the meat after soft separation. Additionally or alternatively, the system may comprise a station to cold pasteurize the meat. Cold pasteurization may be done by irradiation of the raw crab meat. In one embodiment, gamma rays are used. Or, electron beams may be used. Or, X-rays may be used, in one embodiment, this process would generally be conducted in accordance with procedures determined by the manufacture of the irradiation equipment and governmental regulations. In certain embodiments, irradiation before gelation and irradiation after gelation may have different levels of effectiveness. For example, irradiation of the gelled product in a sealed container (i.e., cold pasteurization) may do more to increase shelf life than irradiation prior to being placed in a sealed container.

The system may also comprise a station 53 for mixing the meat with at least one agent that promotes protein binding and gelation. Once the meat has been treated, it may be shaped into a form that allows for use as a finished food product or for further processing including portioning, freezing, refrigerating, cooking and packaging. For example, the meat may be shaped to form rolls that may be processed into nuggets, patties or fillets, or may be sliced into thin sheets (e.g., for use as luncheon meat or pockets). Thus, the system may comprise a station for inserting the treated meat into a container to shape the final product 54. Cold pasteurization (e.g., irradiation of the product in the sealed container or packaging) may also be performed at this point. Once the meat has been mixed with the protein binding agent, and in some cases packaged into a processing container, it may be processed at a station for incubating the meat and the at least one agent to promote gelation 55.

Once the meat has been incubated under conditions that are sufficient for gelation to occur, the meat may then be sent to a station(s) for processing, e.g., slicing and/or packaging 56. Cold pasteurization (e.g., irradiation of the product in the sealed container or packaging) may also be performed after the meat has been packaged. Also, in certain embodiments, the meat may be packaged into the final container upon addition of the protein binding agent, irradiated in that container prior to incubation. Thus, it will be understood that some of the stations as depicted in FIG. 3 may be combined as a single station.

Figure 4:
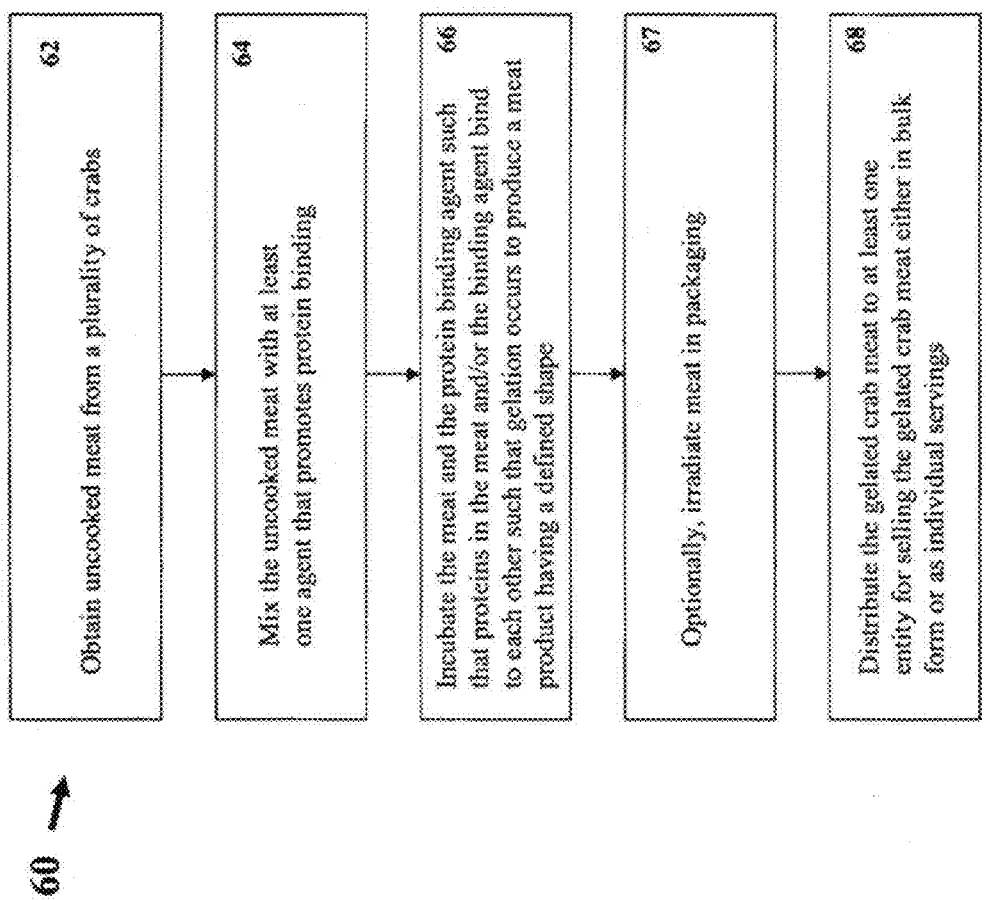
FIG. 4 shows a schematic representation of a method of conducting a business by making raw crab meat food products according to an embodiment of the present invention.

Also, as described herein, the present invention may comprise a method of commercializing the preparation and sale of raw crab meat. FIG. 4 shows an embodiment of such a method 60. For example, in one embodiment, the method may comprise obtaining uncooked meat from a plurality of crabs 62. Also, the method may comprise mixing the uncooked meat with at least one agent that promotes protein binding and gelation 64. Protein binding agents such as those described herein may be used.

The method may also include incubating the meat and the at least one protein binding agent such that the proteins in the binding agent and/or in the meat bind to each other to the extent that gelation occurs. In an embodiment, the meat may be gelled to form distinct shapes, such as a monolithic block or a cylinder 66. In this way, the gelled crab meat may be shaped for sale as a bulk product that may be further processed to provide individual servings. Or, the gelled crab meat may be gelated and packaged as individual servings, or as a collection of individual servings. For example, the gelled crab meat may be cut into patties, and multiple patties packaged as a food product. Also, the gelled crab meat may be irradiated at this point to improve the shelf life 67.

The method may also include distributing the gelated crab meat to at least one entity for selling the gelated crab meat either in bulk form, or as individual servings 68. The gelated crab meat may be distributed refrigerated, on ice, or frozen for long-term storage and use.

The present invention also comprises seafood products made using the methods and systems of the invention. Thus, in one embodiment, the present invention may comprise a processed meat product comprising raw crab meat mixed with at least one protein binding agent. In an embodiment, a portion of the protein binding agent remains as part of the food product.

The protein binding agent may comprise the protein binding agents as described herein. Thus, in an embodiment, the at least one protein binding agent comprises fibrinogen. Alternatively or additionally, the at least one protein binding agent may comprise thrombin. Generally, the thrombin comprises about 1/40, or 1/20, or 1/10, or 1/5 of the fibrinogen. In an embodiment, the thrombin may comprise about 1/20 of the fibrinogen. In alternate embodiments, the fibrinogen and thrombin may (in combination) comprise from 1-20%, 1-10%, or from 2-8%, or from 1-5% or from 4-8% by weight of the weight of the crab meat product.

In alternate embodiments, the Plasma Powder FG based protein binder may comprise from 0.1-10%, or from 0.4-0.7% or from 0.7-1.4% or 1-3%, 1 to 2% or from 2-3% or from 3-5% (by weight) of the crab meat product.

The protein binding agent may, in other embodiments, comprise a transglutaminase (Tgase), and/or a caseinate or other additional non-crab meat proteins. In alternate embodiments, the Tgase-based protein binder may comprise from 0.1-10%, or from 0.75 to 3%, 1 to 2% or from 2-3% or from 3-5% (by weight) of the crab meat product.

Also, in certain embodiments, whey protein or actomyosin may be used, in other embodiments, the protein binding agent may comprise at least one of potato starch, functional pork protein, or functional soy protein concentrate. In alternate embodiments, 0.05-25%, 1-20%, or from 2-15%, or from 3-15% of total product composition may comprise at least one of these other protein binding agents.

Thus, the protein binding agent may comprise from about 0.05-25%, 0.05-20%, 1-20%, 0.1-10%, 0.5-10%, 2-15%, 3-15%, 1-10%, 4-9%, 4-8%, 1-5%, 5-8%, or about 6%, or 0.4-7%, 0.7-1.4%, 1-3%, 0.4-1.4%, 1.4-3%, 0.75-2.5%, 0.05-25%, 0.75 to 3%, 1-2%, 2-3% or 3-5% depending upon the nature of the protein binding agent used.

Embodiments of the present invention may comprise gelated three dimensional semi-rigid semi-solid forms of raw crab meat such as patties, steaks, fillets, nuggets medallions, thin workable sheets, portionable monolithic forms, stuffable pouches and the like. FIG. 5 shows examples of raw crab meat that has been gelled with a protein binding agent to make uncooked patties. For example, FIG. 5, Panel A shows raw crab meat patties 72 that have been cut from a roll 74 of uncooked crab meat that was made using an embodiment of the methods of the present invention. The gelated crab meat shown in FIGS. 5A and 5B may be made by mixing raw crab meat with 5% FIBRIMEX® and allowing the mixture to incubate at 4° C. for 8 hours. The mixture may be shaped to form a roll by stuffing the mixture into a cylindrical container after mixing the uncooked crab meat with the FIBRIMEX®. In an embodiment, the gelated crab meat attains a consistency similar to gelatin. Prior to addition of the protein binding agents, the meat generally has a consistency similar to thick applesauce. In certain embodiments, the gelated meat maintains its shape as a roll when left at room temperature for several hours to several days, and can be cut into patties (e.g., crab medallions).

Figure 5A:
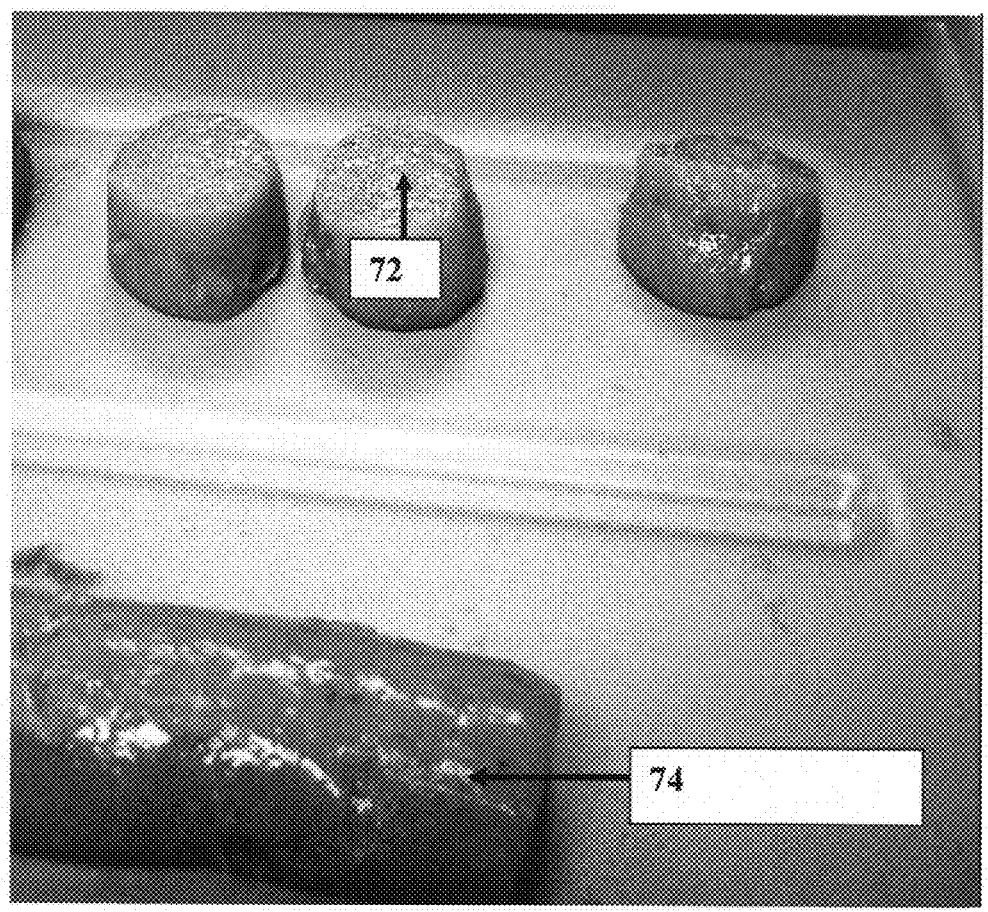
FIG. 5, Panels A-E, shows examples of uncooked crab meat processed by application of protein binding and gelation technology to make a product of the present invention in accordance with alternate embodiments of the present invention.
Figure 5B:
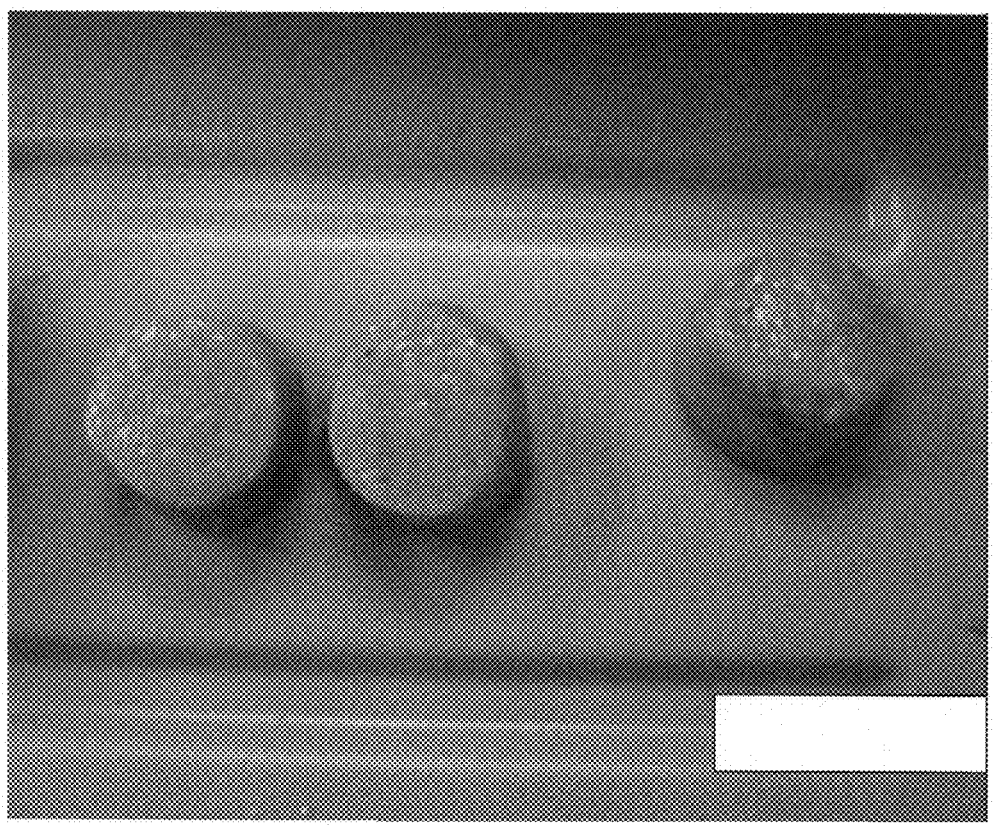
Figure 5C:
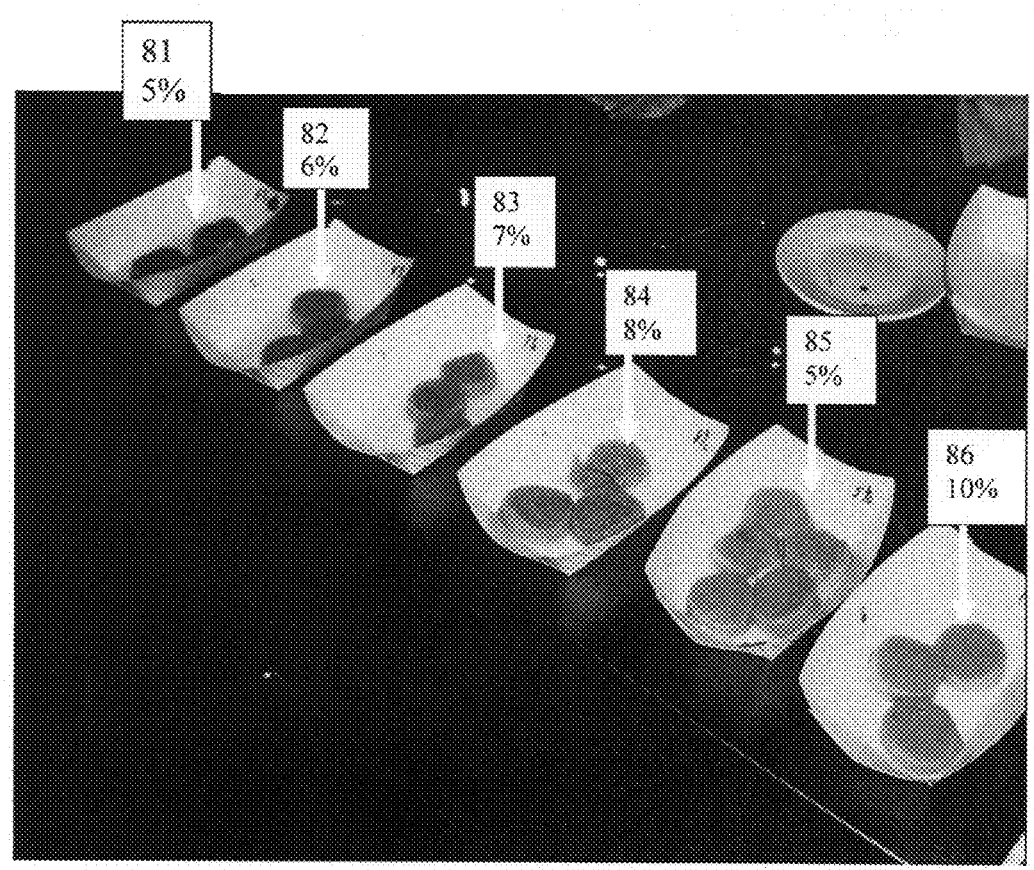

In alternate embodiments, various amounts of the protein binding agent may be used, depending upon the fluidity of the crab meat being processed, the protein binding agent being used, the amount of salt in the meat, the moisture content of the meat, the pH of the meat, the time and temperature used for the incubation, the age of the meat, and other factors. In an embodiment, gelated crab meat may be made by mixing raw crab meat with 5%, 6%, 7%, 8%, 5%, or 10% FIBRIMEX® as indicated, and allowing the mixture to incubate at 4° C. for 6 hours (FIG. 5C). Thus, in certain embodiments, a range of the protein binding agent may be used. In certain embodiments, for a given sample batch of meat of the same age, and moisture content, an increase in rigidity of the gelled product is positively correlated to the amount of protein binding agent used.

Figure 5D:
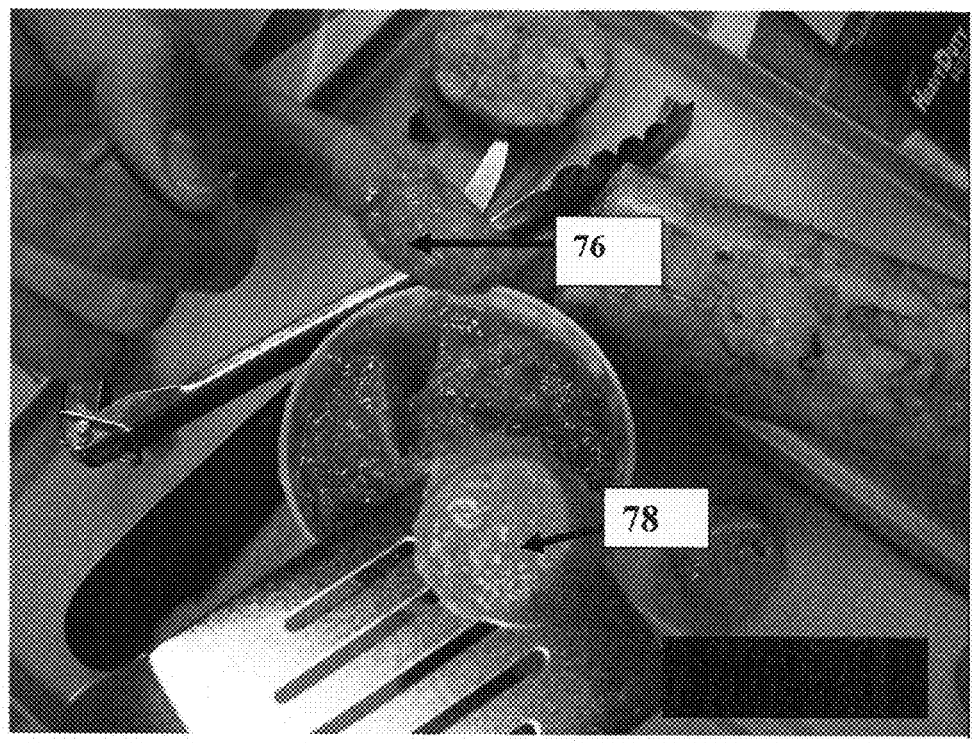

Crab meat is unlike many other meats in that it has an almost liquid consistency in its unprocessed state. In an embodiment, the crab meat has a consistency similar to applesauce prior to addition of the protein binding agent(s). FIG. 5D shows raw crab meat before 76 and after processing 78 with a protein binding agent. The crab meat in FIG. 5D was gelated by incubating with 6% of FIBRIMEX® for 8 hours at 4° C. Thus, in an embodiment, prior to processing the raw crab meat is almost liquid in consistency, whereas after processing the raw crab meat is substantially solid and has a defined cylindrical shape.

Figure 5E:
Figure 6:
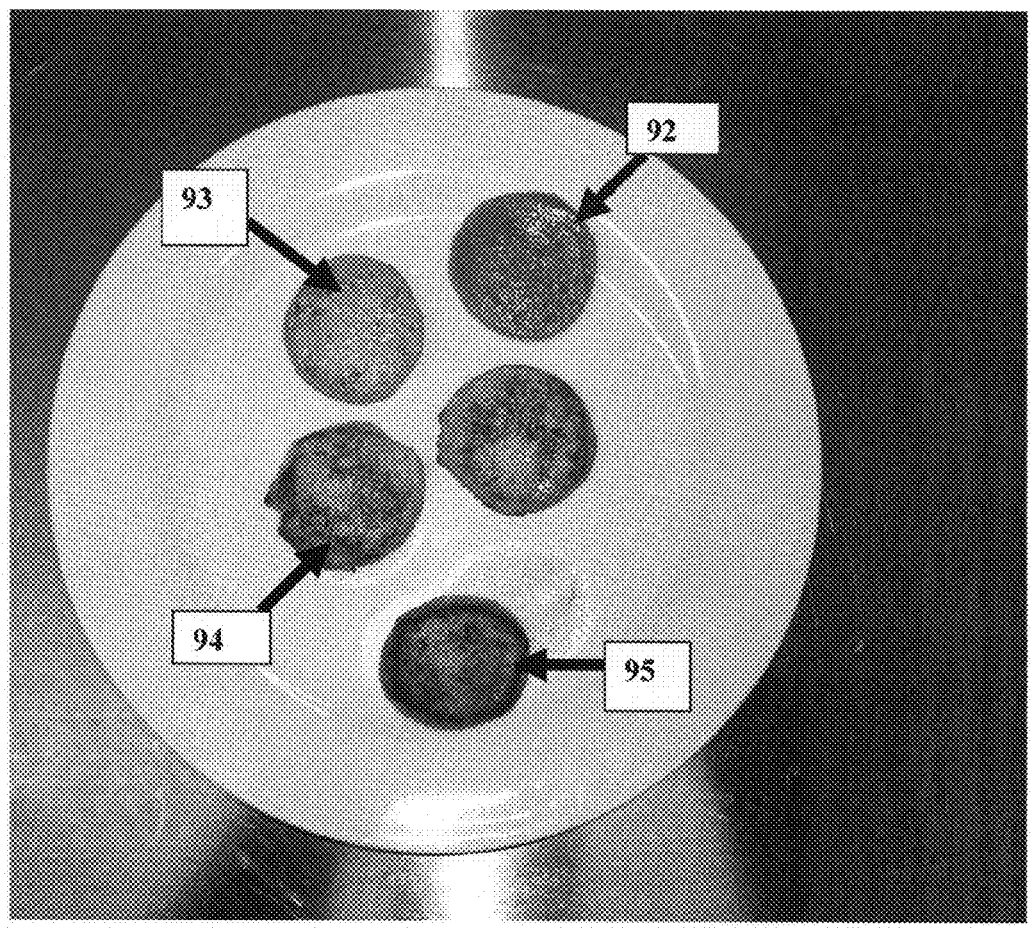
FIG. 6 shows examples of gelated crab meat cut from a cylindrical log in uncooked and cooked form in accordance with alternate embodiments of the present invention.

The gelated uncooked crab meat may be prepared in any number of ways typical of preparing fish or seafood. In one embodiment, the gelated crab meat may be sautéed 79 (FIG. 5E). In various embodiments of the methods, systems and food products of the present invention, the gelated crab meat maintains its shape during cooking. For example, the patties (e.g., medallions) formed by the addition of a protein binding agent may retain their form upon grilling, frying, and/or baking to be served as a unique food product. Thus, as shown in FIG. 6, there may be little shrinkage or change of shape when uncooked crab meat medallions were sautéed for various amounts of time. Shown in FIG. 6 are gelled, uncooked crab meat medallions sliced from a cylinder and completely thawed (i.e., 2 hours at room temperature) 92; a portion of the same gelled crab, slightly "undercooked" (4 minute cook time) 93; a portion of the same gelled crab, cooked for 5 minutes (preferred cook time) 94; and a portion of the same gelled crab, slightly "overcooked" 95. In certain embodiments, even overcooking of the crab meat does not significantly reduce the amount of moisture or change the shape of the food product.

Figure 7A:
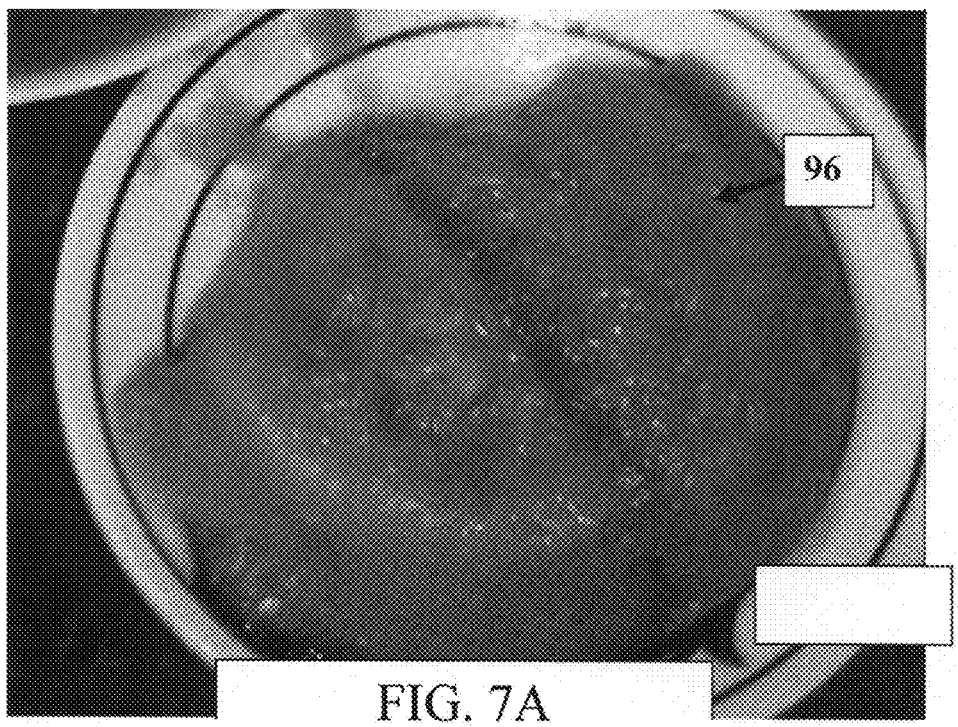
FIG. 7, Panels A-B, shows fillet shaped portions of crab meat cut from a monolithic form of uncooked gelated crab and cooked.
Figure 7B:
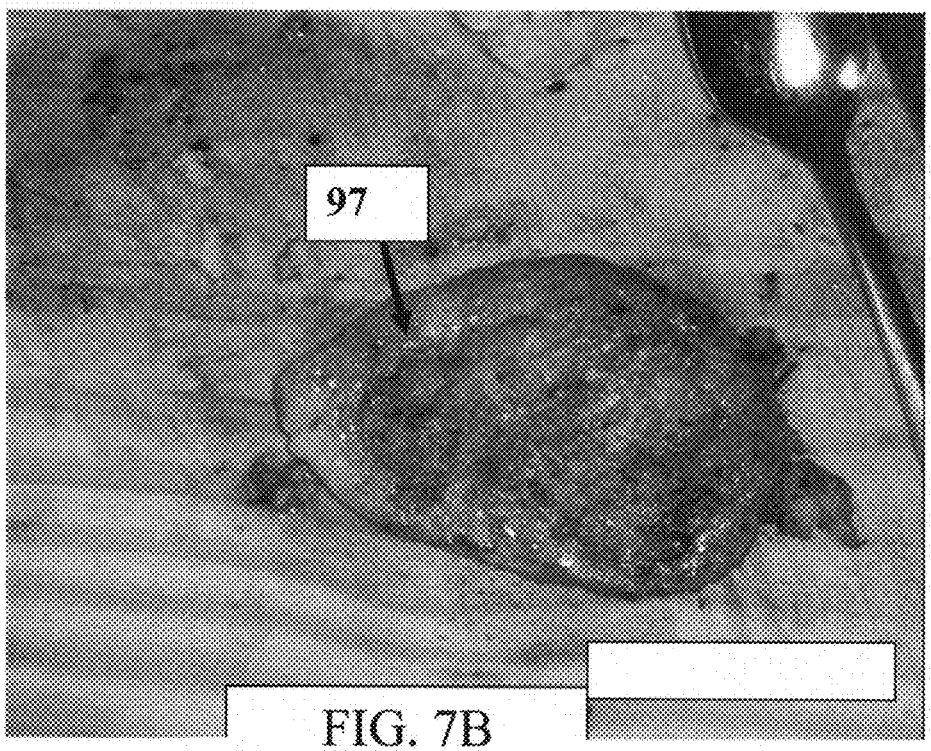

The processed crab meat may be formed into a variety of shapes. In an embodiment, gelated crab meat may be formed in a pint sized container (i.e., about 3-5 inches in diameter) (FIG. 7). Once the crab meat has gelled, slices may be cut, thereby providing a portion similar to a fillet of meat or fish 96 (FIG. 7A). The fillet may then be fried (sautéed), grilled or baked 97 (FIG. 7B) to provide a unique food product—a crab meat fillet.

Certain embodiments of the present invention may comprise certain advantages. For example, in one embodiment, the present invention may provide uncooked crab meat in a form that may be processed into food products of desired shape. Also, in certain embodiments, the processed meat products of the present invention increase the culinary applications for the meat. For example, the meat may be prepared as a medallion for appetizers, or as a patty for sandwiches, or as a fillet.

As another advantage, in certain embodiments, the processed meat products of the present invention may exhibit very little to no loss of the meat upon cooking. This can allow for consistency in the preparation of recipes using the crab meat products.

Also, in certain embodiments, the processed meat products may display the same or similar texture and/or juiciness as non-processed meat products when served raw, or upon cooking. Additionally, in certain embodiments, the processed meat products may display the same or similar taste as non-processed meat products when eaten raw, or upon cooking.

Certain embodiments of the invention may comprise certain economic advantages. For example, in an embodiment the product may provide a plurality of new food products and thereby expand the market for crab meat to include uncooked crab meat. Also, in certain embodiments, the system may materially increase the yields associated with processing crabs. In certain embodiments, the system may materially increase the ability to utilize crabs as a natural resource.

EXAMPLES

Example 1

Preparation of Crab Meat Rolls and Patties Derived from Such Rolls

The methods may be used to make gelated three dimensional semi-rigid semi-solid forms such as patties, steaks, fillets, nuggets, medallions, thin workable sheets (e.g., stuffable pouches), monolithic forms that may be subdivided into individual portions, and the like. FIG. 5 shows examples of raw crab meat that have been gelled with a protein bonding agent to make uncooked patties. For example. FIG. 5, Panels A, B, and C, shows raw crab meat that has been treated with a protein bonding agent FIBRIMEX® and shaped to form a roll. The gelated crab meat shown in FIGS. 5A and 5B was made by mixing raw crab meat with 6% FIBRIMEX® and allowing the mixture to incubate at 4° C. for 8 hours. The mixture was shaped to form a roll by hand-mixing raw crab meat that was extracted using a soft separator with 6% by weight FIBRIMEX® and then hand-filling a tube-shaped plastic casing with the mixture within 5 minutes of mixing. The casing was then clamped shut and placed in a refrigerated environment to incubate. After incubation, the log (gelated crab-filled casing) was frozen at −10 degrees F. Later, the log was thawed and the casing removed, at which time medallions were cut from the log an cooked. It was found that the gelated crab meat displayed a consistency similar to gelatin. The meat maintained its shape as a roll when left at room temperature, and could be cut into patties (e.g., crab medallions).

FIG. 5C shows an experiment where gelated crab meat was made by mixing raw crab meat with 5%, 6%, 7%, 8%, 5%, or 10% FIBRIMEX® as indicated, and allowing the mixture to incubate at 4° C. for 6 hours, it was found that in general, the rigidity of gelled samples increased with an increase in the percentage of protein binder used.

FIG. 5D shows raw crab meat before 76 and after processing 78 with a protein bonding agent. The crab meat in FIG. 5D was gelated by incubating with 8% of FIBRIMEX® for 8 hours at 4° C. Thus, it can be seen that prior to processing the raw crab meat is almost liquid in consistency, whereas after processing the raw crab meat has a defined cylindrical shape.

FIG. 5E shows crab meat medallions made as described above for FIGS. 5A and 5B being sautéed. It can be seen that the gelated crab meat holds it shape when heated or cooked.

Example 2

Stability of Treated Crab Meat to Cooking and Other Culinary Preparation

FIG. 6 shows round portions cut from as gelated cylinder at varying stages of preparation. The gelated crab meat shown in FIG. 6 was made by mixing raw crab meat with 5% FIBRIMEX® and allowing the mixture to incubate at 4° C. for 6 hours. The mixture was shaped to form a roll by hand-mixing raw crab meat that was extracted using a soft separator in a plastic tub with 5% by weight FIBRIMEX® and then hand-filling a plastic casing with the mixture within 5 minutes of mixing. The casing was then clamped shut and placed in a refrigerated environment to incubate. After incubation the log (gelated crab-filled casing) was frozen at −10 degrees F. Later the log was thawed and the casing removed, at which time medallions were cut from the log an cooked. It was found that the gelated crab meat maintained its shape during cooking. Thus, as shown in FIG. 6, there was little shrinkage or change of shape when uncooked crab meat medallions were sautéed for various amounts of time. Shown in FIG. 6 are gelled, uncooked crab meat medallions sliced from a cylinder and completely thawed (i.e., 2 hours at room temperature) 92; a portion of the same gelled crab, slightly "undercooked" (4 minute cook time) 93; a portion of the same gelled crab, cooked for 5 minutes (preferred cook time) 94; and a portion of the same gelled crab, slightly "overcooked" 95. It can be seen that even overcooking of the crab meat does not significantly reduce the amount of moisture or change the shape of the food product. Thus, the patties (e.g., medallions) formed by the addition of a protein binding agent retained their form (even after over-cooking) and could be served as a unique food product.

Example 3

Crab Meat Fillets

FIG. 7A shows gelated crab meat gelled to a monolithic form in a pint-sized container. The gelated crab meat shown in FIG. 7A was made by mixing raw crab meat with 7% FIBRIMEX® and allowing the mixture to incubate at 4° C. for 8 hours. The extracted raw crab meat was mixed with 7% FIBRIMEX by weight in a plastic pint size container having dimensions of about a 4 inch top diameter, 3.5 inch bottom diameter and a height of about 3 inches. After mixing the container served as a mold for the gelation process and was incubated for 8 hours at 4 degrees Celsius. Once the meat had gelled, it was removed from the contained and a fillet portion was sectioned off of the formed gelated meat by knife. FIG. 7B shows the fillet after being sautéed. Thus, the experiment shows an example of a never-before described food product, a crab meat fillet.

Example 4

Viscosity Measurement of Gelated Raw Crab

Experiments were performed to quantify the nature of the gelation of the raw crab meat. In these experiments, gelated crab meat that had been made essentially as described in Example 1 (raw crab meat was incubated with various amounts of FIBRIMEX for at least 8 hours at 4° C.). The gelated crab was then frozen and stored for a period of time. In this experiment, raw crab meat from various parts of the crab, and that had been stored frozen for various periods of time was analyzed for the change in viscosity upon gelation. Sample 1 corresponds to crab meat that was obtained from the body of a crab, and then was stored frozen for about 6 months; Sample 2 corresponds to corresponds to crab meat obtained from the body of a crab and then stored frozen for about 17 months; Samples 3 and 4 corresponds to two different samples of crab meat that was obtained from the claws of a crab, and then stored frozen for about 6 months. For each sample (1, 2, 3 or 4). A corresponds to the thawed and untreated sample, and B correspond to the sample that was gelated with the indicated amounts of FIBRIMEX®. Samples were incubated with the FIBRIMEX® for 8 hours at 4° C. Results of the analysis of changes in viscosity (in centipoise, cP) as measured at increasing levels of sheer stress (RPM) using a Dial Rading Viscometer (Brookfield Engineering, Model RVF, Serial #69050) are shown in Table 1. It was found that under static conditions, the untreated raw crab meat displayed pseudo-plastic characteristics (i.e., behaved as a fluid), whereas the gelated crab meat displayed plastic characteristics (i.e., behaved as a substantially solid material). It can be seen that the increase in viscosity ranged from about 16 to 37 fold for sample 1; form about 1.2 to 2.7 fold for sample 2; from about 2.2 to 5.2 fold for sample 3; and from about 1.5 to 4.2 fold for sample 4. Based on the results, both the treated and untreated crab meat displayed non-Newtonian characteristics, in that the ratio of shear stress and shear rate (F'/S) was not a constant.

Additionally, as shown by comparing samples 3 and 4, where claw meat obtained from the same sample was treated with different amounts of the binding agent, there appeared to be a greater increase in viscosity upon using more of the protein binding agent (FIBRIMEX®).

It was also found that the meat that had been stored frozen for a longer period of time displayed less change upon gelation, indicating that the integrity of the proteins found in the raw crab meat (at least for the purposes of gelation) may be decrease over long, periods in storage. The increase in viscosity ranged from about 16 to 37 fold for the treated body meat of sample 1, whereas the older body meat in sample 2 displayed a higher base level viscosity (perhaps due to protein denaturation) and less relative change in viscosity for each of the shear stress levels tested.

TABLE 1

Viscosity Testing of Gelated Raw Crab

| Sample # A-pre gelation B-post gelation | Sample Temp Fahrenheit | Viscosity (centipoise) @ Shear Stress Static | Viscosity (centipoise) @ Shear Stress 2 RPM | Viscosity (centipoise) @ Shear Stress 4 RPM | Viscosity (centipoise) @ Shear Stress 10 RPM | Viscosity (centipoise) @ Shear Stress 20 RPM |
| --- | --- | --- | --- | --- | --- | --- |
| 1-A Body No Additive | 45 degrees | Psuedo-plastic | 42,000 cP | 22,500 cP | 13,800 cP | 10,200 cP |
| 1-B Body 7% Fibrin | 45 degrees | Plastic | 1,580,000 cP | 730,000 cP | 284,000 cP | 160,000 cP |
| 2-A Body No Additive | 46 degrees | Pseudo-plastic | 215,000 cP | 127,000 cP | 64,500 cP | 35,500 cP |
| 2-B Body 10% Fibrin | 46 degrees | Plastic | 600,000 cP | 270,000 cP | 96,000 cP | 42,000 cP |
| 3-A Claw No Additive | 44 degrees | Pseudo-plastic | 134,000 cP | 82,000 cP | 38,400 cP | 27,500 cP |
| 3-B Claw 8% Fibrin | 46 degrees | Plastic | 700,000 cP | 350,000 cP | 120,000 cP | 60,000 cP |
| 4-A Claw No Additive | 44 degrees | Pseudo-plastic | 115,000 cP | 72,500 cP | 40,000 cP | 25,500 cP |
| 4-B Claw 5% Fibrin | 48 degrees | Plastic | 480,000 cP | 220,000 cP | 80,000 cP | 38,000 cP |

It will be understood that each of the elements described above, or two or more together, may also find utility in applications different from the types described. While the invention has been illustrated and described as crab meat food products and methods and systems for making such products, it is not intended to be limited to the details shown, since various modifications and substitutions can be made without departing in any way from the spirit of the present invention. As such, further modifications and equivalents of the invention disclosed herein may occur to persons skilled in the art using no more than routine experimentation, and all such modifications and equivalents are believed to be within the spirit and scope of the invention as described herein.

That which is claimed is:

1. An uncooked crab meat product comprising:
   (a) uncooked crab meat; and
   (b) at least one protein binding agent comprising fibrinogen and thrombin that promotes protein binding, wherein the at least one protein binding agent is mixed with the uncooked crab meat in an amount such that proteins in the meat and/or in the protein binding agent bind to each other to the extent that gelation of the crab meat occurs to form a gelated uncooked crab meat product;
   wherein the gelated uncooked crab meat product comprises an increased viscosity in comparison to the uncooked crab meat prior to gelation wherein the uncooked meat product is in one or more forms selected from the group consisting, of patties, steaks, fillets, nuggets, medallions, thin workable sheets, and stuffable pouches.

2. The uncooked crab meat product of claim 1, wherein one or more of molds, casings or packaging is used to shape the uncooked crab meat product.

3. The uncooked crab meat product of claim 1, wherein the protein binding agent comprises about 0.05-20% of the gelated uncooked crab meat product.

4. The uncooked crab meat product of claim 1, wherein the protein binding agent comprises about 0.10-10% of the gelated uncooked crab meat product.

5. The uncooked crab meat product of claim 1, wherein the protein binding agent comprises about 1-10% of the gelated uncooked crab meat product.

6. The uncooked crab meat product of claim 1, wherein the protein binding agent comprises about 4-9% of the gelated uncooked crab meat product.

7. The uncooked crab meat product of claim 1, wherein the protein binding agent comprises about 0.4-1.4% of the gelated uncooked crab meat product.

8. The uncooked crab meat product of claim 1, wherein the protein binding agent comprises about 1.4-3% of the gelated uncooked crab meat product.

9. The uncooked crab meat product of claim 1, wherein the protein binding agent comprises about 0.75-2.5% of the gelated uncooked crab meat product.

10. The uncooked crab meat product of claim 1, wherein the uncooked crab meat product is in the form of a fillet.

11. The uncooked crab meat product of claim 10, wherein the uncooked crab meat product is fried, grilled or baked.

12. The uncooked crab meat product of claim 1, wherein the at least one protein binding agent comprises transglutaminase.

13. The uncooked crab meat product of claim 1, wherein the gelated uncooked crab meat product further comprises one or more additives.

14. The uncooked crab meat product of claim 13, wherein the additive is one or more members selected from the group consisting of salts, fillers, buffers, other animal proteins, other vegetable proteins, and other compounds that may support the gelation method.

15. The uncooked crab meat product of claim 1, wherein the uncooked crab meat comprises crab from the Infraorder Brachyura or the Infraorder Anomura.

16. The uncooked crab meat product of claim 1, wherein the gelated meat comprises an increase in viscosity.

17. The uncooked crab meat product of claim 1, wherein the increase in viscosity is at least 100% as measured at a shear stress of 2 revolutions per minute (RPM).

18. A method for reducing costs and/or producing higher yields of an uncooked crab meat product wherein the uncooked crab meat product is to be used in food products comprising the steps of:
   (a) obtaining uncooked meat from a crab by soft separation;
   (b) mixing the uncooked meat with at least one protein binding agent comprising fibrinogen and thrombin that promotes binding of protein in the uncooked crab meat; and
   (c) incubating, the uncooked crab meat and the at least one protein binding agent under conditions such that proteins in the uncooked crab meat and in the protein binding agent bind to each other to the extent that gelation of the uncooked crab meat occurs; wherein the gelated uncooked crab meat product comprises an increased viscosity in comparison to the uncooked crab meat prior to gelation.

19. The method of claim 18, wherein the uncooked crab meat and the at least one protein binding agent are incubated under conditions to produce a meat product that comprises a substantially solid form.

20. The method of claim 19, wherein the substantially solid form is suitable for direct culinary use or mass processing.

21. An uncooked crab meat product comprising:
   (a) uncooked crab meat; and
   (b) at least one protein binding agent comprising transglutaminase that promotes protein binding, wherein the at least one protein binding agent is mixed with the uncooked crab meat in an amount such that proteins in the meat and/or in the protein binding agent bind to each other to the extent that gelation of the crab meat occurs to form a gelated uncooked crab meat product;
   wherein the gelated uncooked crab meat product comprises an increased viscosity in comparison to the uncooked crab meat prior to gelation.

22. The uncooked crab meat product of claim 21, wherein the uncooked meat product is in one or more forms selected from the group consisting of patties, steaks, fillets, nuggets, medal lions, thin workable sheets, and stuffable pouches.

23. The uncooked crab meat product of claim 22, wherein one or more of molds, casings or packaging is used to shape the uncooked crab meat product.

24. The uncooked crab meat product of claim 21, wherein the protein binding agent comprises about 0.05-20% of the gelated uncooked crab meat product.

25. The uncooked crab meat product of claim 21, wherein the protein binding agent comprises about 0.10-10% of the gelated uncooked crab meat product.

26. The uncooked crab meat product of claim 21, wherein the protein binding agent comprises about 1-10% of the gelated uncooked crab meat product.

27. The uncooked crab meat product of claim 21, wherein the protein binding agent comprises about 4-9% of the gelated uncooked crab meat product.

28. The uncooked crab meat product of claim 21, wherein the protein binding, agent comprises about 0.4-1.4% of the gelated uncooked crab meat product.

* * * * *